(12) United States Patent
Shi et al.

(10) Patent No.: US 11,215,545 B2
(45) Date of Patent: Jan. 4, 2022

(54) DEVICES AND METHODS FOR CELL ANALYSIS

(71) Applicant: CYTOCHIP INC., Irvine, CA (US)

(72) Inventors: Wendian Shi, Irvine, CA (US);
Zhaokai Meng, Irvine, CA (US);
Yuzhe Ding, Irvine, CA (US)

(73) Assignee: CytoChip Inc., Irvine, CA (US)

( * ) Notice: Subject to any disclaimer, the term of this patent is extended or adjusted under 35 U.S.C. 154(b) by 203 days.

(21) Appl. No.: 16/619,735

(22) PCT Filed: Jun. 12, 2018

(86) PCT No.: PCT/US2018/037114
§ 371 (c)(1),
(2) Date: Dec. 5, 2019

(87) PCT Pub. No.: WO2018/231835
PCT Pub. Date: Dec. 20, 2018

(65) Prior Publication Data
US 2020/0158615 A1    May 21, 2020

Related U.S. Application Data

(60) Provisional application No. 62/519,467, filed on Jun. 14, 2017.

(51) Int. Cl.
*G01N 15/02*    (2006.01)
*G01N 15/14*    (2006.01)
(Continued)

(52) U.S. Cl.
CPC ..... *G01N 15/0205* (2013.01); *G01N 15/1436* (2013.01); *G01N 15/1459* (2013.01);
(Continued)

(58) Field of Classification Search
CPC .......... G01N 15/0205; G01N 15/1434; G01N 15/1436; G01N 15/1459;
(Continued)

(56) References Cited

U.S. PATENT DOCUMENTS 5,596,456 A      1/1997 Luecke
2009/0325217 A1  12/2009 Luscher
(Continued)

OTHER PUBLICATIONS

Extended European Search Report, dated Mar. 1, 2021, 9 pages, issued in European Application No. 18817543.4.
(Continued)

*Primary Examiner* — Jennifer Wecker
*Assistant Examiner* — Kathryn Elizabeth Limbaugh
(74) *Attorney, Agent, or Firm* — Avant Law Group, LLC

(57) ABSTRACT

The disclosure provides devices, device systems, and methods for analyzing cells (e.g., blood cells) or particles in a sample. In some embodiments, the disclosure provides various devices and device systems including: a light source; a collecting lens; and one, two, or more detectors. In other embodiments, the devices and device systems include a flow cell or a cartridge device with a flow cell. In further embodiments, the disclosure provides various methods including the steps of: using a light source to emit an irradiation light; using the irradiation light to illuminate a sample flow; using a collecting lens to collect both scattered light and fluorescent light from the sample flow; and using one, two, or more detectors to detect the collected scattered light and fluorescent light. Optionally, these methods include using a flow cell to form a sample flow.

19 Claims, 17 Drawing Sheets

Side View

(51) Int. Cl.
    *G01N 33/52*     (2006.01)
    *G01N 15/00*     (2006.01)
    *G01N 15/10*     (2006.01)

(52) U.S. Cl.
    CPC ..... *G01N 33/52* (2013.01); *G01N 2015/0073* (2013.01); *G01N 2015/1006* (2013.01); *G01N 2015/1087* (2013.01); *G01N 2015/1493* (2013.01)

(58) Field of Classification Search
CPC ... G01N 2015/0073; G01N 2015/1006; G01N 2015/1087; G01N 2015/1493; G01N 33/52
See application file for complete search history.

(56) References Cited

U.S. PATENT DOCUMENTS

| | | |
|---|---|---|
| 2011/0235030 A1 | 9/2011 | Champseix et al. |
| 2015/0330963 A1 | 11/2015 | Vidal et al. |
| 2016/0356722 A1 | 12/2016 | Glezer et al. |
| 2017/0030824 A1 | 2/2017 | Takeuchi et al. |
| 2017/0045437 A1 | 2/2017 | Ishimaru |

OTHER PUBLICATIONS

PCT Appln. No. PCT/US2018/037114, International Preliminary Reporton Patentability, dated Dec. 17, 2019, 9 pages.

Side View

Side View

DEVICES AND METHODS FOR CELL ANALYSIS

CROSS REFERENCE TO RELATED APPLICATIONS

This application is the United States national stage entry under 35 U.S.C. 371 of PCT/US2018/037114 filed on Jun. 12, 2018, and further claims priority to U.S. Provisional Patent Application No. 62/519,467 filed on Jun. 14, 2017, the disclosure of which are incorporated by reference herein in their entireties.

FIELD OF THE DISCLOSURE

The disclosure relates generally to the field of medicine, cytometry, and medical devices. More specifically, the disclosure relates to the field of medical devices and methods for cell analysis.

BACKGROUND

All publications cited herein are incorporated by reference in their entirety to the same extent as if each individual publication or patent application was specifically and individually indicated to be incorporated by reference. The following description includes information that may be useful in understanding the present disclosure. It is not an admission that any of the information provided herein is prior art or relevant to the presently disclosure, or that any publication specifically or implicitly referenced is prior art.

Flow cytometry is a powerful method for detecting cells in a sample and analyzing their characteristics with high throughput. By forming a sample flow in a flow cell and irradiating the sample flow with light from a light source, signals such as scattered light in forward angle, scatted light in side angle, and fluorescence can be detected from individual cells, and can be used to analyze their characteristics such as cell size, cell granularity, cellular nucleic acids, cellular membrane integrity, and cellular antigen expressions, etc.

In clinical applications, flow cytometry has been widely used for detecting and analyzing cells in human or animal blood, such as enumerating the number of blood cells; classifying blood cells into diverse types (e.g., white blood cells, red blood cells and platelet cells); and analyzing cellular antigen expressions (e.g., $CD4^+$ antigen, $CD8^+$ antigen, etc.). For example, in hematology analysis, flow cytometry has been used to measure the total counts of white blood cells, red blood cells and platelet cells per sample volume, and to further classify white blood cells into different subtypes (e.g., lymphocytes, monocytes, neutrophils, eosinophils, and basophils) and determine their respective percentages. For another example, flow cytometry is used in AIDS diagnostics for counting the number of $CD4^+$ lymphocyte cells and $CD8^+$ lymphocyte cells in blood.

Traditional analyzers for flow cytometry analysis normally have a fixed flow cell to form the sample flow. The alignment between the flow cell and optical detection components is fixed and has no deviation. On the contrary, in analyzers having a replaceable or disposable flow cell, the alignment between the flow cell and optical detection components may have significant deviation when the flow cell is replaced each time. This alignment deviation becomes a prominent issue for analyzers in which the flow cell is disposed and replaced after each sample measurement.

Furthermore, the flow cell in traditional analyzers normally has at least two optical transparent surfaces for signal detection, where one surface is used for measuring scattered light with a forward angle (e.g., a scattering angle less than about 20 degrees) from the sample flow and the other surface is used for measuring scattered light with a side angle (e.g., a scattering angle more than about 70 degrees), fluorescence, or both from the sample flow. However, in some analyzers, the flow cell (e.g., some low-cost flow cells made by plastic injection molding process) may have only one optical transparent surface for signal detection. Low-cost replaceable or disposable flow cells are necessary for many applications such as point-of-care diagnostics. But flow cells having only one optical transparent surface for signal detection may limit the options of detectable signals.

Additionally, the replaceable or disposable flow cell is normally built into a cartridge device, and the cartridge device's surfaces or any other surface in the optical path can reflect light back into the light source and introduce undesired noise. Also, the intensity of the light signals detected from a target (e.g., particles and cells) in the replaceable or disposable flow cell can be weak, and hence it is challenging to improve the collection efficiency of the light signals.

To address these challenges, the present disclosure provides various devices and methods for analyzing particles and cells.

SUMMARY

The following presents a simplified summary of the invention in order to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

To address those challenges as discussed above, the present disclosure provides various devices and methods for analyzing particles and cells. In various embodiments, this disclosure provides various devices and methods for analyzing cells in blood samples. In various embodiments, these device and methods can also be used for analyzing other particles (e.g., beads, nanoparticles, protein molecules, nucleic acid molecules, etc.) in a sample. In various embodiments, these devices and methods are suitable for replaceable or disposable flow cells. In various embodiments, these devices and methods are suitable for flow cells having only one optical transparent surface for signal detection and measurement. In various embodiments, these devices and methods are also compatible for other flow cells, for example, fixed flow cells and flow cells having more than one optical transparent surface for signal detection and measurement.

Various embodiments of the present disclosure provide a device or device system that comprises: a light source configured to emit an irradiation light for illuminating a sample flow, wherein the sample flow comprises particles and/or cells; a collecting lens configured to collect both a scattered light with a forward angle and a fluorescent light from the particles and/or cells in the sample flow; and one, two, or more detectors configured to detect a signal of the scattered light with a forward angle and a signal of the fluorescent light. A device or device system as disclosed herein can be used for analyzing particles and/or cells in a sample.

Various embodiments of the present disclosure provide a device or device system that comprises: a flow cell configured to form a sample flow of a measurement sample, wherein the measurement sample comprises particles and/or cells; a light source configured to emit an irradiation light for illuminating the sample flow; a collecting lens configured to collect both a scattered light with a forward angle and a fluorescent light from the particles and/or cells in the sample flow; and one, two, or more detectors configured to detect a signal of the scattered light with a forward angle and a signal of the fluorescent light. A device or device system as disclosed herein can be used for analyzing particles and/or cells in a sample.

Various embodiments of the present disclosure provide a method of analyzing particles and/or cells in a sample flow, comprising: using a light source to emit an irradiation light; using the irradiation light to illuminate the sample flow; using a collecting lens to collect both a scattered light with a forward angle and a fluorescent light from the particles and/or cells in the sample flow; and using one, two, or more detectors to detect a signal of the scattered light with a forward angle and a signal of the fluorescent light.

Various embodiments of the present disclosure provide a method of analyzing particles and/or cells in a measurement sample, comprising: using a flow cell to form a sample flow of the measurement sample; using a light source to emit an irradiation light; using the irradiation light to illuminate the sample flow; using a collecting lens to collect both a scattered light with a forward angle and a fluorescent light from the particles and/or cells in the sample flow; and using one, two, or more detectors to detect a signal of the scattered light with a forward angle and a signal of the fluorescent light.

Various embodiments of the present disclosure provide a device or device system that comprises: a light source configured to emit an irradiation light for illuminating a sample flow, wherein the sample flow comprises particles and/or cells; a collecting lens configured to collect both a scattered light with a side angle and a fluorescent light from the particles and/or cells in the sample flow; and one, two, or more detectors configured to detect a signal of the scattered light with a side angle and a signal of the fluorescent light. A device or device system as disclosed herein can be used for analyzing particles and/or cells in a sample.

Various embodiments of the present disclosure provide a device or device system that comprises: a flow cell configured to form a sample flow of a measurement sample, wherein the measurement sample comprises particles and/or cells; a light source configured to emit an irradiation light for illuminating the sample flow; a collecting lens configured to collect both a scattered light with a side angle and a fluorescent light from the particles and/or cells in the sample flow; and one, two, or more detectors configured to detect a signal of the scattered light with a side angle and a signal of the fluorescent light. A device or device system as disclosed herein can be used for analyzing particles and/or cells in a sample.

Various embodiments of the present disclosure provide a method of analyzing particles and/or cells in a sample flow, comprising: using a light source to emit an irradiation light; using the irradiation light to illuminate the sample flow; using a collecting lens to collect both a scattered light with a side angle and a fluorescent light from the particles and/or cells in the sample flow; and using one, two, or more detectors to detect a signal of the scattered light with a side angle and a signal of the fluorescent light.

Various embodiments of the present disclosure provide a method of analyzing particles and/or cells in a measurement sample, comprising: using a flow cell to form a sample flow of the measurement sample; using a light source to emit an irradiation light; using the irradiation light to illuminate the sample flow; using a collecting lens to collect both a scattered light with a side angle and a fluorescent light from the particles and/or cells in the sample flow; and using one, two, or more detectors to detect a signal of the scattered light with a side angle and a signal of the fluorescent light.

Various embodiments of the present disclosure provide method for analyzing particles and/cells in a sample, comprising: receiving the sample into a cartridge device comprising a flow cell; using the cartridge device to mix the sample the sample with a reagent to form a measurement sample; using the flow cell to form a sample flow of the measurement sample; using a light source to emit an irradiation light; using the irradiation light to illuminate the sample flow; using a collecting lens to collect both a scattered light and a fluorescent light from the particles and/or cells in the sample flow; and using one, two, or more detectors to detect a signal of the scattered light and a signal of the fluorescent light. In some embodiments, the scattered light comprises a forward scattered light, that is, a scattered light with a forward angle (e.g., a scattering angle less than about 25 degrees). In other embodiments, the scattered light comprises a side scattered light, that is, a scattered light with a side angle (e.g., a scattering angle more than about 25 degrees).

BRIEF DESCRIPTION OF THE DRAWINGS

Illustrative embodiments of the present disclosure are described in detail below with reference to the attached drawing figures.

DETAILED DESCRIPTION

Figure 1A:
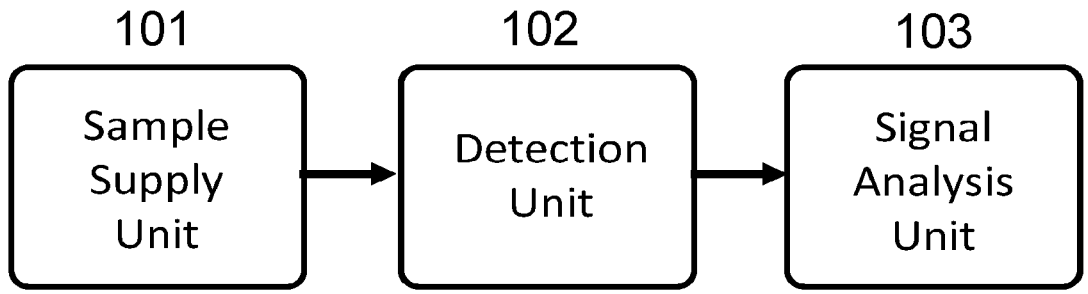
FIG. 1A illustrates, in accordance with various embodiments of the disclosure, one non-limiting example of a device or device system as disclosed herein, which comprises a sample supply unit, a detection unit, and a signal analysis unit.

The following describes some non-limiting exemplary embodiments of the invention with references to the accompanying drawings. The described embodiments are merely a part rather than all of the embodiments of the invention. All other embodiments obtained by a person of ordinary skill in the art based on the embodiments of the disclosure shall fall within the scope of the disclosure.

All references cited herein are incorporated by reference in their entirety as though fully set forth. Unless defined otherwise, technical and scientific terms used herein have the same meaning as commonly understood by one of ordinary skill in the art to which this disclosure belongs. Tabelling, *Introduction to Microfluidics reprint edition*, Oxford University Press (2010); Hguyen et al., *Fundamentals and Applications of Microfluidics* $2^{nd}$ ed., Artech House Incorporated (2006); Berg et al., *Microfluidics for Medical Applications*, Royal Society of Chemistry (2014); Gomez et al., *Biological Applications of Microfluidics* $1^{st}$ ed., Wiley- Interscience (2008); and Colin et al., *Microfluidics* 1$^{st}$ ed., Wiley-ISTE (2010), provide one skilled in the art with a general guide to many of the terms used in the present application.

One skilled in the art will recognize many methods and materials similar or equivalent to those described herein, which could be used in the practice of the present disclosure. Other features and advantages of the disclosure will become apparent from the following detailed description, taken in conjunction with the accompanying drawings, which illustrate, by way of example, various features of embodiments of the disclosure. Indeed, the present disclosure is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this disclosure belongs. It should be understood that this disclosure is not limited to the particular methodology, devices, systems, protocols, and reagents, etc., described herein and as such can vary. The definitions and terminology used herein are provided to aid in describing particular embodiments, and are not intended to limit the claims.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

Various embodiments of the present disclosure provide a device or device system that comprises: a light source configured to emit an irradiation light for illuminating a sample flow, wherein the sample flow comprises particles and/or cells; a collecting lens configured to collect both a scattered light with a forward angle and a fluorescent light from the particles and/or cells in the sample flow; and one, two, or more detectors configured to detect a signal of the scattered light with a forward angle and a signal of the fluorescent light. A device or device system as disclosed herein can be used for analyzing particles and/or cells in a sample.

Various embodiments of the present disclosure provide a device or device system that comprises: a flow cell configured to form a sample flow of a measurement sample, wherein the measurement sample comprises particles and/or cells; a light source configured to emit an irradiation light for illuminating the sample flow; a collecting lens configured to collect both a scattered light with a forward angle and a fluorescent light from the particles and/or cells in the sample flow; and one, two, or more detectors configured to detect a signal of the scattered light with a forward angle and a signal of the fluorescent light. A device or device system as disclosed herein can be used for analyzing particles and/or cells in a sample.

Various embodiments of the present disclosure provide a device or device system that comprises: a light source configured to emit an irradiation light for illuminating a sample flow, wherein the sample flow comprises particles and/or cells; a collecting lens configured to collect both a scattered light with a side angle and a fluorescent light from the particles and/or cells in the sample flow; and one, two, or more detectors configured to detect a signal of the scattered light with a side angle and a signal of the fluorescent light. A device or device system as disclosed herein can be used for analyzing particles and/or cells in a sample.

Various embodiments of the present disclosure provide a device or device system that comprises: a flow cell configured to form a sample flow of a measurement sample, wherein the measurement sample comprises particles and/or cells; a light source configured to emit an irradiation light for illuminating the sample flow; a collecting lens configured to collect both a scattered light with a side angle and a fluorescent light from the particles and/or cells in the sample flow; and one, two, or more detectors configured to detect a signal of the scattered light with a side angle and a signal of the fluorescent light. A device or device system as disclosed herein can be used for analyzing particles and/or cells in a sample.

In various embodiments, a device or device system as described herein further comprises a focusing module configured to focus the irradiation light to form an elliptical beam spot on the sample flow. In various embodiments, a device or device system as described herein further comprises a receiving module configured to split the scattered light and the fluorescent light collected by the collecting lens into two separate optical paths toward two separate detectors, respectively. In various embodiments, a device or device system as described herein further comprises a doublet lens configured to focus the collected fluorescent light. In various embodiments, a device or device system as described herein further comprises a signal analysis unit configured to analyze the signal of the scattered light and the signal of the fluorescent light for analyzing the particles and/or cells.

Various embodiments of the present disclosure provide a method of analyzing particles and/or cells in a sample flow, comprising: using a light source to emit an irradiation light; using the irradiation light to illuminate the sample flow; using a collecting lens to collect both a scattered light with a forward angle and a fluorescent light from the particles and/or cells in the sample flow; and using one, two, or more detectors to detect a signal of the scattered light with a forward angle and a signal of the fluorescent light.

Various embodiments of the present disclosure provide a method of analyzing particles and/or cells in a measurement sample, comprising: using a flow cell to form a sample flow of the measurement sample; using a light source to emit an irradiation light; using the irradiation light to illuminate the sample flow; using a collecting lens to collect both a scattered light with a forward angle and a fluorescent light from the particles and/or cells in the sample flow; and using one, two, or more detectors to detect a signal of the scattered light with a forward angle and a signal of the fluorescent light. In some embodiments, two separate detectors are used to detect the signal of the scattered light with a forward angle and the signal of the fluorescent light. In various embodiments, the method further comprises using a focusing module to focus the irradiation light to form an elliptical beam spot on the sample flow. In various embodiments, the method further comprises using a receiving module to split the scattered light with a forward angle and the fluorescent light collected by the collecting lens into two separate optical paths toward two separate detectors, respectively. In various embodiments, the method further comprises using a doublet lens to focus the collected fluorescent light. In various embodiments, the method further comprises using a signal analysis unit to analyze the signal of the scattered light with a forward angle and the signal of the fluorescent light for analyzing the particles and/or cells.

Various embodiments of the present disclosure provide a method of analyzing particles and/or cells in a sample flow, comprising: using a light source to emit an irradiation light; using the irradiation light to illuminate the sample flow; using a collecting lens to collect both a scattered light with a side angle and a fluorescent light from the particles and/or cells in the sample flow; and using one, two, or more detectors to detect a signal of the scattered light with a side angle and a signal of the fluorescent light.

Various embodiments of the present disclosure provide a method of analyzing particles and/or cells in a measurement sample, comprising: using a flow cell to form a sample flow of the measurement sample; using a light source to emit an irradiation light; using the irradiation light to illuminate the sample flow; using a collecting lens to collect both a scattered light with a side angle and a fluorescent light from the particles and/or cells in the sample flow; and using one, two, or more detectors to detect a signal of the scattered light with a side angle and a signal of the fluorescent light. In some embodiments, two separate detectors are used to detect the signal of the scattered light with a side angle and the signal of the fluorescent light. In various embodiments, the method further comprises using a focusing module to focus the irradiation light to form an elliptical beam spot on the sample flow. In various embodiments, the method further comprises using a receiving module to split the scattered light with a side angle and the fluorescent light collected by the collecting lens into two separate optical paths toward two separate detectors, respectively.

In various embodiments, the method further comprises using a doublet lens to focus the collected fluorescent light. In various embodiments, the method further comprises using a signal analysis unit to analyze the signal of the scattered light with a side angle and the signal of the fluorescent light for analyzing the particles and/or cells.

Various embodiments of the present disclosure provide method for analyzing particles and/cells in a sample, comprising: receiving the sample into a cartridge device comprising a flow cell; using the cartridge device to mix the sample the sample with a reagent to form a measurement sample; using the flow cell to form a sample flow of the measurement sample; using a light source to emit an irradiation light; using the irradiation light to illuminate the sample flow; using a collecting lens to collect both a scattered light and a fluorescent light from the particles and/or cells in the sample flow; and using one, two, or more detectors to detect a signal of the scattered light and a signal of the fluorescent light. In some embodiments, the scattered light comprises a forward scattered light, that is, a scattered light with a forward angle (e.g., a scattering angle less than about 25 degrees). In other embodiments, the scattered light comprises a side scattered light, that is, a scattered light with a side angle (e.g., a scattering angle more than about 25 degrees). In various embodiments, two separate detectors are used to detect the signal of the scattered light and the signal of the fluorescent light. In various embodiments, the method further comprises using a focusing module to focus the irradiation light to form an elliptical beam spot on the sample flow. In various embodiments, the method further comprises using a receiving module to split the scattered light and the fluorescent light collected by the collecting lens into two separate optical paths toward two separate detectors, respectively. In various embodiments, the method further comprises using a doublet lens to focus the collected fluorescent light. In various embodiments, the method further comprises using a signal analysis unit to analyze the signal of the scattered light and the signal of the fluorescent light for analyzing the particles and/or cells.

In various embodiments, the light source comprises a laser diode, a light-emitting diode (LED), a laser module, or a halogen lamp, or a combination thereof. In some embodiments, the light source comprises a laser diode and an optical fiber.

In various embodiments, the collecting lens comprises a spherical lens, an aspherical lens, or a doublet lens, or a combination thereof. In some embodiments, the collecting lens is a spherical lens. In some embodiments, the collecting lens is an aspherical lens. In some embodiments, the collecting lens is a doublet lens.

In various embodiments, a device or device system as disclosed herein comprises two separate detectors: one is configured to detect the signal of the scattered light with a forward angle and the other is configured to detect the signal of the fluorescent light. In various embodiments, a device or device system as disclosed herein comprises two separate detectors: one is configured to detect the signal of the scattered light with a side angle and the other is configured to detect the signal of the fluorescent light.

In various embodiments, a device or device system as disclosed herein comprises a first detector configured to detect the signal of the scattered light with a forward angle, and a second detector configured to detect the signal of the fluorescent light. In various embodiments, a device or device system as disclosed herein comprises a first detector configured to detect the signal of the scattered light with a side angle, and a second detector configured to detect the signal of the fluorescent light. In accordance with the present disclosure, the terms "first" and "second" are used to identify different detectors and they do not indicate any sequential relationship.

In various embodiments, the detector for the fluorescent light comprises a photodiode, an avalanche photodiode, or a silicon photomultiplier, or a combination thereof.

In various embodiments, the collected scattered light includes a forward scattered light with a scattering angle less than about 3, 4, 5, 6, 7, 8, 9, 10, 11, 12, 13, 14, 15, 16, 17, 18, 19, 20, 21, 22, 23, 24, or 25 degrees. In various embodiments, the detected forward scattered light includes a scattered light with a scattering angle less than about 3, 4, 5, 6, 7, 8, 9, 10, 11, 12, 13, 14, 15, 16, 17, 18, 19, 20, 21, 22, 23, 24, or 25 degrees.

In various embodiments, the collected scattered light includes a side scattered light with a scattering angle more than about 25, 30, 35, 40, 45, 50, 55, 60, 65, 70, 75, 80, 85, or 90 degrees. In various embodiments, the detected scattered light includes a side scattered light with a scattering angle more than about 25, 30, 35, 40, 45, 50, 55, 60, 65, 70, 75, 80, 85, or 90 degrees.

In various embodiments, a device or device system as described herein further comprises a focusing module.

In some embodiments, the focusing module is configured to focus the irradiation light to form an elliptical beam spot on the sample flow. In some embodiments, the focusing module comprises a lens that is either not coaxial or not perpendicular with the central axis of irradiation light.

In various embodiments, the elliptical beam spot has a width larger than the width of the flow cell. In various embodiments, the elliptical beam spot covers more than the whole width of the flow cell. In various embodiments, the major axis ($d_2$) of the elliptical beam spot is perpendicular to the direction of the sample flow and the minor axis ($d_1$) of the elliptical beam spot is along the direction of the sample flow. In various embodiments, the $d_2:d_1$ ratio is more than 1 or in the range of about 2-5, 5-10, 10-15, 15-20, or 20-25.

In various embodiments, the major axis ($d_2$) of the elliptical beam spot is larger than the width ($d_3$) of the flow cell. In various embodiments, the $d_2:d_3$ ratio is in the range of about 2-5, 5-10, 10-15, 15-20, or 20-25.

In various embodiments, the elliptical beam spot on the flow cell has a diameter of about 4-5, 5-10, 10-20, 20-30, 30-40, 40-50, 50-60, 60-70, 70-80, 80-90, 90-99, or 99-100 µm in the direction parallel to the sample flow, and a diameter of about 40-100, 100-500, 500-1000, 1000-1500, 1500-2000, 2000-2500, 2500-3000, 3000-3500, 3500-4000, 40004500, or 4500-5000 µm in the direction perpendicular to the sample flow. In some embodiments, the elliptical beam spot on the flow cell has a diameter of about 15-16, 16-20, 20-30, 30-40, or 40-50 µm in the direction parallel to the sample flow, and a diameter of about 150-160, 160-200, 200-500, 500-1000, 1000-1500, 1500-2000, or 2000-2500 µm in the direction perpendicular to the sample flow.

In various embodiments, the sample flow formed in the flow cell has a width of about 4-5, 5-10, 10-20, 20-30, 30-40, 40-50, 50-60, 60-70, 70-80, 80-90, or 90-100 µm in the direction perpendicular to the sample flow. In some embodiments, the sample flow formed in the flow cell has a width of about 20-30, 30-40, or 40-50 µm in the direction perpendicular to the sample flow.

In various embodiments, the flow cell has a width of about 4-5, 5-10, 10-20, 20-30, 30-40, 40-50, 50-60, 60-70, 70-80, 80-90, or 90-100 µm in the direction perpendicular to the sample flow. In some embodiments, the flow cell has a width of about 20-30, 30-40, or 4050 µm in the direction perpendicular to the sample flow. In various embodiments, the flow cell has a width in the range of about 1-10, 10-40, 40-100, or 100-200 µm; and a depth in the range of about 1-10, 10-40, 40-100, or 100-200 µm. In various embodiments, the flow cell has a length in the range of about 1-10, 10-100, 100-1,000, 1,000-5,000 µm, or 5,000-10,000 µm.

In some embodiments, the flow cell is configured to form the sample flow without a sheath flow. In other embodiments, the flow cell is configured to form the sample flow with a sheath flow. In some embodiments, the sample flow has no sheath flow. In other embodiments, the sample flow is surrounded by a sheath flow.

In various embodiments, the flow cell comprises a surface that is illuminated by the irradiation light, and the surface is positioned to be not perpendicular with the central axis of the irradiation light. In some embodiments, the angle between the surface and the central axis of the irradiation light can be about 45-50, 50-55, 55-60, 60-65, 65-70, 70-75, 75-80, 8085, 85-89, or 89-89.9 degrees.

In various embodiments, the flow cell is part of a cartridge device configured to be placed into a reader instrument for analysis, and wherein the reader instrument comprises a light source, a collecting lens, detectors, and a signal analysis unit. In various embodiments, the cartridge device comprises a surface that is illuminated by the irradiation light, and the surface is positioned to be not perpendicular with the central axis of the irradiation light. In some embodiments, the angle between the surface and the central axis of the irradiation light can be about 45-50, 50-55, 55-60, 60-65, 65-70, 70-75, 75-80, 80-85, 85-89, or 89-89.9 degrees.

In various embodiments, the flow cell or the cartridge device that hosts the flow cell is positioned or titled in such an orientation that a reflective surface of the flow cell or the cartridge device is not perpendicular to the central axis of the irradiation light and directs the reflected light away from the light source. In certain embodiments, the angle between such a reflective surface and the central axis of the irradiation light can be about 45-50, 50-55, 5560, 60-65, 65-70, 70-75, 75-80, 80-85, 85-89, or 89-89.9 degrees.

In some other embodiments, a lens in the focusing module is positioned or titled in such an orientation that a reflective surface of the lens is not perpendicular to the central axis of the irradiation light and directs the reflected light away from the light source. In certain embodiments, the angle between such a reflective surface and the central axis of the irradiation light can be about 45-50, 50-55, 55-60, 60-65, 65-70, 70-75, 75-80, 80-85, 85-89, or 89-89.9 degrees.

In various embodiments, the cartridge device is configured to mix a sample with a reagent to form the measurement sample and to form a sample flow of the measurement sample in the flow cell. In various embodiments, a method as described herein further comprises using the cartridge device to mix a sample with a reagent to form the measurement sample and to form a sample flow of the measurement sample in the flow cell. In various embodiments, the reagent comprises a fluorescent labeling compound, an osmolality-adjusting compound, a sphering compound, or a lysing compound, or a combination thereof. Non-limiting examples of the reagent can be found in the present disclosure and U.S. patent application Ser. No. 15/819,416, which are incorporated herein by reference in their entirety as if fully set forth.

In various embodiments, the reagent comprises a fluorescent labeling compound. In various embodiments, the fluorescent labeling compound comprises an antibody conjugated with a fluorophore, an antibody conjugated with a fluorescent particle, or a fluorescent dye, or combination thereof. In various embodiments, the reagent comprises a fluorescent dye.

In various embodiments, a device or device system as described herein further comprises a receiving module.

In various embodiments, the receiving module is configured to split the scattered light with a forward angle and the fluorescent light collected by the collecting lens into two separate optical paths toward two separate detectors, respectively. In various embodiments, the receiving module is configured to split the scattered light with a side angle and the fluorescent light collected by the collecting lens into two separate optical paths toward two separate detectors, respectively. In various embodiments, the receiving module comprises a beam splitter, a dichroic mirror, a prism, or a diffractive grating, or a combination thereof. In some embodiments, the receiving module comprise a doublet lens configured to focus the collected fluorescent light.

In various embodiments, a device or device system as described herein further comprises a doublet lens configured to focus the collected fluorescent light.

In various embodiments, a device or device system as described herein further comprises a signal analysis unit configured to analyze the signal of the scattered light with a forward angle and the signal of the fluorescent light for analyzing the particles and/or cells.

In various embodiments, the measurement sample comprises blood cells. In various embodiments, the sample comprises blood cells.

In various embodiments, analyzing the particles and/or cells comprises analyzing blood cells. In various embodiments, analyzing blood cells comprises one or more of: measuring the number and/or percentage of white blood cells, identifying white blood cells into subtypes (e.g., lymphocytes, monocytes, neutrophils, eosinophils, and basophils), measuring the number and/or percentage of a subtype of white blood cells, measuring the number and/or percentage of red blood cells, and measuring the number and/or percentage of platelets. In some embodiments, analyzing blood cells comprises measuring the number of red blood cells and the number of platelets.

Figure 1B:
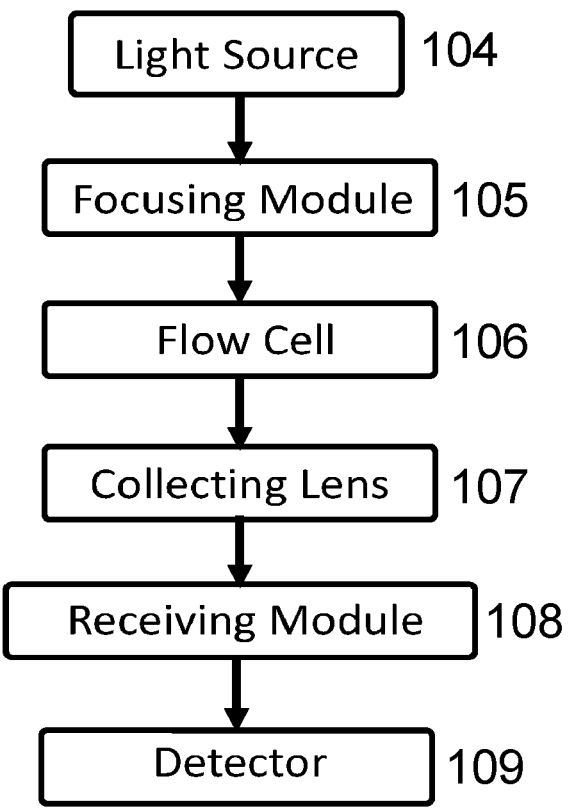
FIG. 1B illustrates, in accordance with various embodiments of the disclosure, one non-limiting example of a detection unit, which comprises a light source, a focusing module, a flow cell, a collecting lens, a receiving module, and a detector.

In various embodiments, a device or device system as disclosed herein comprises a sample supply unit 101, a detection unit 102, and a signal analysis unit 103, as shown in FIG. 1A. The sample supply unit provides to the detection unit a measurement sample containing cells, or particles, or both. In various embodiments, the detection unit comprises a light source 104, a focusing module 105, a flow cell 106, a collecting lens 107, a receiving module 108, and a detector 109, as shown in FIG. 1B. The sample supply unit provides a measurement sample to the flow cell of the detection unit. The measurement sample is passed through the flow cell to form a sample flow. Light emitted from the light source is used to irradiate the sample flow and light signals from the sample flow (e.g., scattered light with a forward angle, fluorescence, or both) are measured by the detector. Before irradiating the sample flow, the light emitted from the light source is shaped into a desired beam spot by the focusing module. Before being measured by the detector, the light signals from the sample flow are collected by the collecting lens and directed by the receiving module towards the detector. The signal analysis unit analyzes the light signals measured by the detector to obtain desired results (e.g., the number of cells, characteristics of individual cells, and the distribution and characterization of cell populations in the measurement sample). The receiving module can be used for various other functions: to separate the collected light into multiple optical paths, to filter out certain wavelengths from the collected light, to focus the collected light into a target spot of particular size or shape, or to perform other light processing functionalities. In various embodiments, one, two, or more detectors can be used for measuring one, two, or more types of light signals from the sample flow.

Figure 2A:
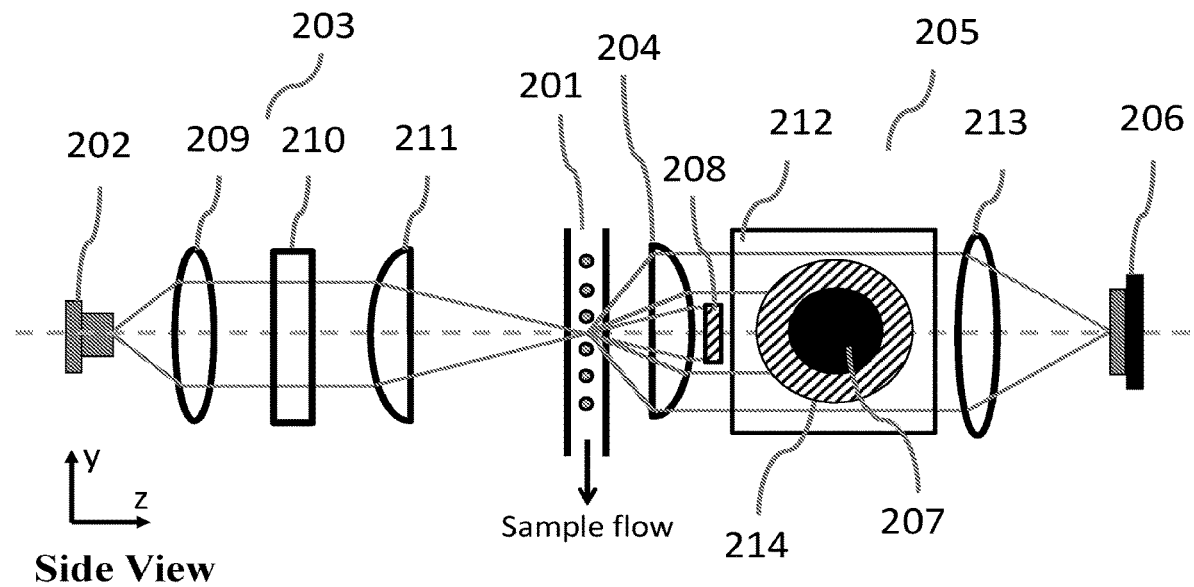
FIGS. 2A and 2B illustrate, in accordance with various embodiments of the disclosure, a non-limiting example of the detection unit, in which a flow cell is used to form the sample flow of the measurement sample.
Figure 2B:
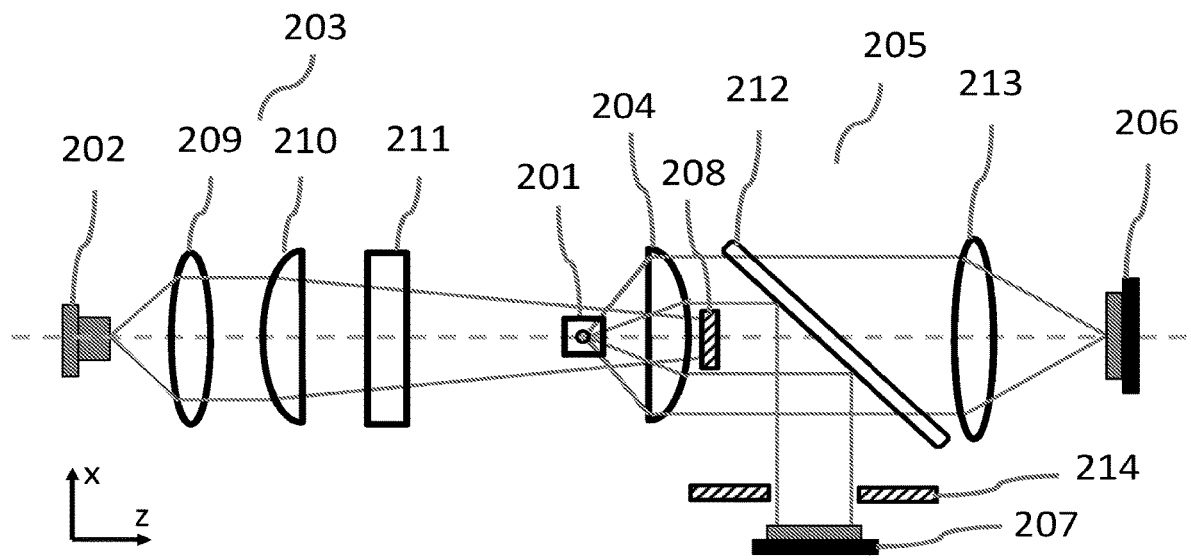

FIG. 2A (side view) and FIG. 2B (top view) show a non-limiting example of the detection unit, in which a flow cell 201 is used to form the sample flow of the measurement sample. A light source 202 emits an irradiation light to irradiate the sample flow. A focusing module 203 focuses and shapes the irradiation light into a particular beam shape on the sample flow. A collecting lens 204 collects both scattered light with a forward angle and fluorescence from the sample flow illuminated with the irradiation light. A receiving module 205 separates the collected light into two optical paths. Two detectors, detector 206 and detector 207, detect and measure the collected light on the two optical paths. A beam stopper 208 can be positioned in the optical path between the flow cell and one of the detectors and blocks the irradiation light that passes through the flow cell.

In this non-limiting example, the focusing module 203 comprises a condenser lens 209, and two cylindrical lenses 210 and 211. The irradiation light emitted from the source 201 is collimated by the condenser lens 209 and forms parallel light with either a circular beam shape or an elliptical beam shape. The irradiation light further passes through the cylindrical lenses 210 and 211. The two cylindrical lenses are positioned in such an orientation that the cylinder axis of the lens 210 and the cylinder axis of the lens 211 are perpendicular to each other. The flow cell 201 is positioned at or close to the focal point of the lens 211 and away from the focal point of the lens 210, where the irradiation light is focused and shaped into a light beam with an elliptical shape on the sample flow.

The collecting lens 204 is a condenser lens and the flow cell 201 can be positioned at or close to its focal point. The signal from the measurement sample is collected and condensed by the collecting lens 204 before entering the receiving module 205. The collected signal includes but is not limited to scattered light with a forward angle and fluorescence from the sample flow. The signal from the measurement sample is collimated with the collecting lens 204 into parallel light. Furthermore, a beam stopper 208 can be positioned behind the collecting lens 204 to block the irradiation light from entering the receiving module.

The receiving module 205 comprises a dichroic mirror 212, which is tilted at a 45-degree angle relative to the collected parallel light. The dichroic mirror 212 is a long-pass dichroic mirror, which reflects the light with a wavelength below a designated threshold. The scattered light from the sample flow has a wavelength that is the same or close to the irradiation light. The fluorescence from the sample flow has a wavelength spectrum including wavelengths longer than the irradiation light. By choosing a dichroic mirror with a threshold wavelength that is longer than the irradiation light but shorter than the desired fluorescence, it separates the scattered light and the fluorescence into two optical paths. Alternatively, the receiving module can use other optical configurations (e.g., a beam splitter, a combination of a beam splitter and optical filters, a prism, a diffractive grating, etc.) to separate the scattered light and the fluorescence. In this example, a condenser lens 213 is positioned in front of the detector 206, and condenses the light passing through the dichroic mirror on the detector. The light reflected by the dichroic mirror is received in the detector 207. An aperture 214 made with an opaque material and having a transparent opening in the center can be positioned in front of the detector 207. The aperture 214 blocks the light outside the transparent opening from entering the detector 207.

The collecting lens 204 in the detection unit is used to collect both the scattered light with a forward angle and the fluorescence from the sample flow. In some embodiments, the collected scattered light comprises light with a scattering angle less than about 20 degrees. In some embodiments, the collected scattered light comprises light with a scattering angle less than about 15 degrees. In some embodiments, the collected scattered light comprises light with a scattering angle less than about 10 degrees. In some embodiments, the collected scattered light comprises light with a scattering angle less than about 5 degrees. In some embodiments, the collected scattered light comprises light with a scattering angle less than about 4 degrees. In some embodiments, the collected scattered light comprises light with a scattering angle less than about 3 degrees. In some embodiments, the collected scattered light comprises light from elastic scattering. In some embodiments, the collected scattered light comprises light from non-elastic scattering. In various embodiments, the collecting lens is a spherical lens, an aspherical lens, or a doublet lens, or a combination thereof.

In traditional analyzers, such as the one described in U.S. Pat. No. 7,580,120, the scattered light with a forward angle and the fluorescence are not collected in the same collecting lens; instead, the scattered light with a forward angle is collected in one collecting lens and the fluorescence is collected in another collecting lens. The lens collecting the fluorescence is positioned perpendicular to the direction of the irradiation light, and thus collects only scattered light with a side angle, which usually having a scattering angle more than about 70 degrees. This configuration requires the flow cell to have at least two optical transparent surfaces, one for the collection of the scattered light with a forward angle and the other for the collection of the fluorescence signals.

On the contrary, by collecting the fluorescence and the scattered light with a forward angle in the same collecting lens, one optical transparent surface is sufficient for the detection of both signals. In low-cost flow cells, such as those built with plastic injection molding, it is more cost-effective to have one optical transparent surface than two optical transparent surfaces.

Figure 3A:
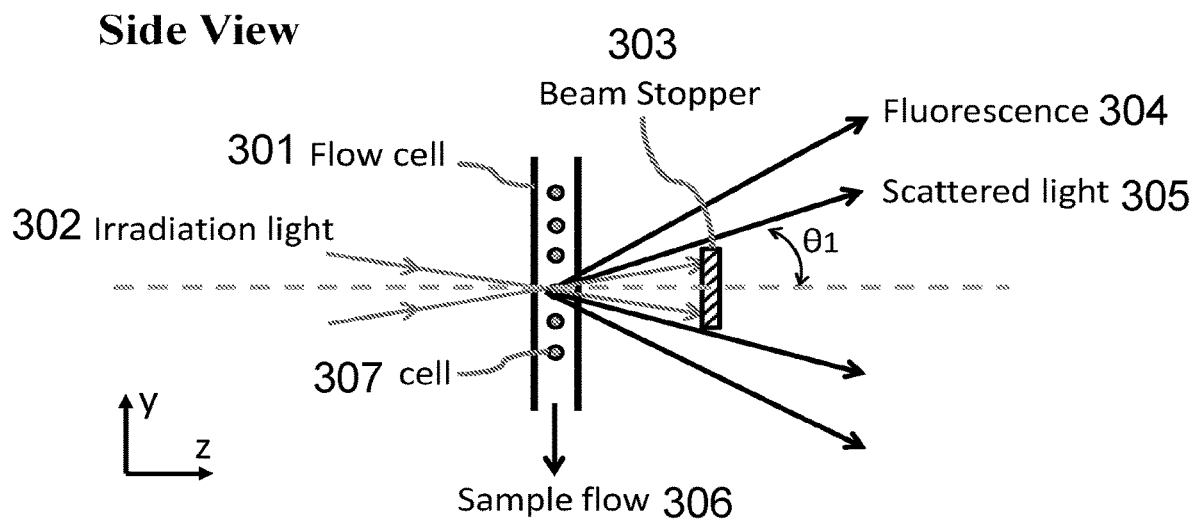
FIG. 3A illustrates, in accordance with various embodiments of the disclosure, that when blocking the irradiation light, the beam stopper also blocks the scattered light with a scattering angle less than $\theta_1$.
Figure 3B:
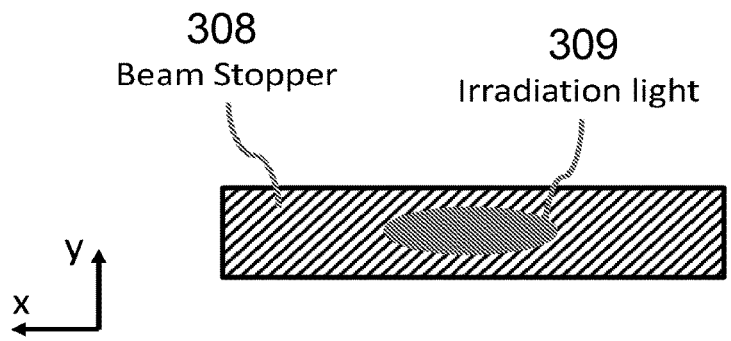
FIG. 3B illustrates, in accordance with various embodiments of the disclosure, that the beam stopper can be a light obstruction bar comprising opaque material.

The intensity of the fluorescence and the scattered light could be significantly lower than the intensity of the irradiation light. In order to detect signals with satisfactory signal-to-noise ratio (SNR), therefore, it is desirable to remove the irradiation light from the collected light. In the non-limiting example of FIG. 2A and FIG. 2B, a beam stopper 208 is used to block the irradiation light behind the flow cell. When blocking the irradiation light 302, as shown in FIG. 3A, the beam stopper 303 also blocks the scattered light 305 with a scattering angle less than $\theta_1$. The value $\theta_1$ is adjustable by the size and shape of the beam stopper 303, as well as the distance from the beam stopper 303 to the sample flow 301. In a non-limiting example as shown in FIG. 3B, the beam stopper 308 can be a light obstruction bar comprising opaque material. The size of bar is designated to be larger than the beam spot of the irradiation light 309 at the position of the beam stopper. In some embodiments, the beam stopper has a surface that minimizes the reflection of the irradiation light to reduce stray light in the detection unit. Examples of the surface include but are not limited to surfaces made with light absorptive materials (e.g., black painting, and anodized aluminum), etc.

Figure 4A:
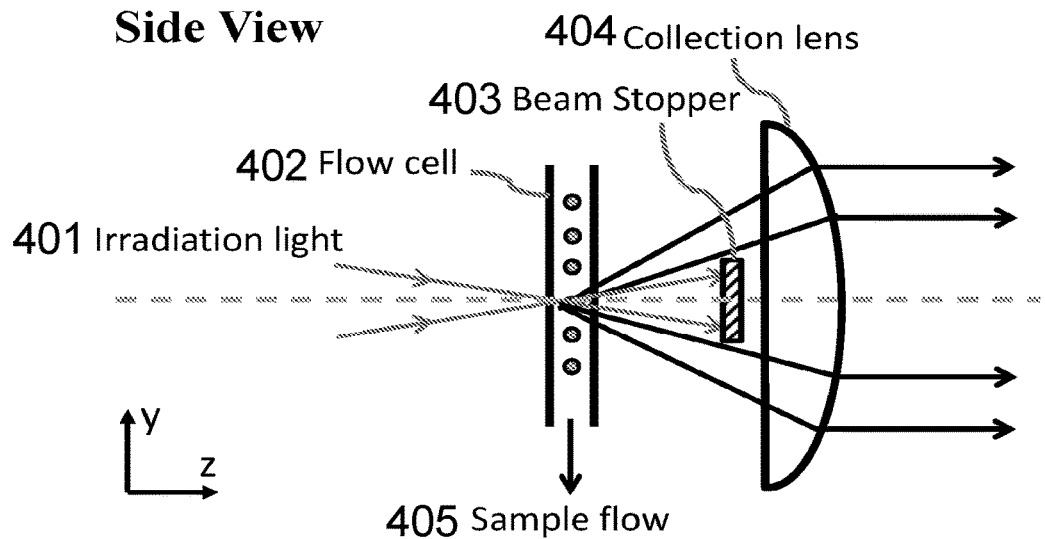
FIG. 4A illustrates, in accordance with various embodiments of the disclosure, that the beam stopper can be positioned between the flow cell and the collecting lens.
Figure 4B:
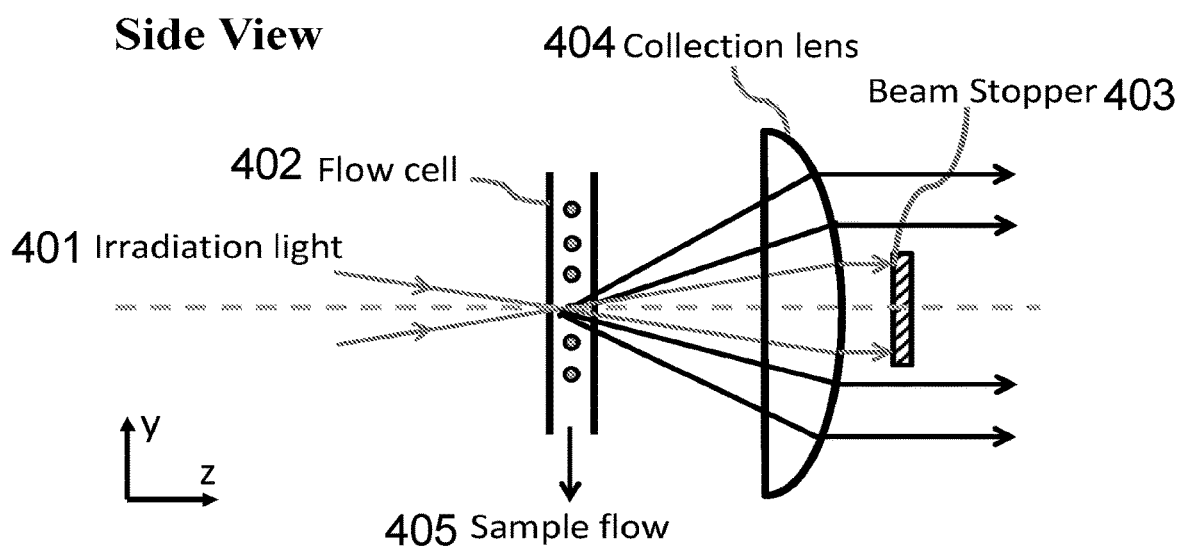
FIG. 4B illustrates, in accordance with various embodiments of the disclosure, that the beam stopper can be positioned behind the collecting lens.

The beam stopper is positioned in the optical path between the flow cell and one of the detectors to block the irradiation light. In a non-limiting example of FIG. 4A, the beam stopper 403 is positioned between the flow cell 405 and the collecting lens 404. In another non-limiting example of FIG. 4B, the beam stopper 403 is positioned behind the collecting lens 405.

In some embodiments, it is advantageous to position the beam stopper behind the collecting lens. To collect the fluorescence from the sample flow, it is preferred that the collecting lens is close in distance to the flow cell, so as to enlarge the collection angle of the fluorescence. If the beam stopper is positioned between the flow cell and the collecting lens, then the distance from the sample flow to the beam stopper is limited, and a given size of the beam stopper may block the scattered light with a significantly large $\theta_1$. By positing the beam stopper behind the collecting lens, it increases the distance from the sample flow to the beam stopper, without sacrificing the distance from the sample flow to the collecting lens. In this way, the angle $\theta_1$ could be reduced for a given size of the beam stopper. In some embodiments, the collecting lens itself may have a thickness in the range of 5-15 mm. This lens thickness could help to add considerable distance between the sample flow and the beam stopper.

Figure 5A:
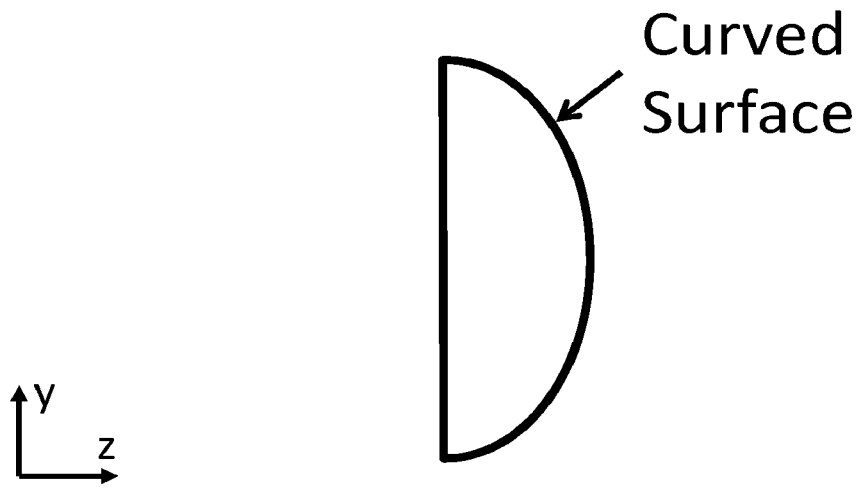
FIG. 5A illustrates, in accordance with various embodiments of the disclosure, that a spherical lens has at least one curved surface that has a spherical shape.
Figure 5B:
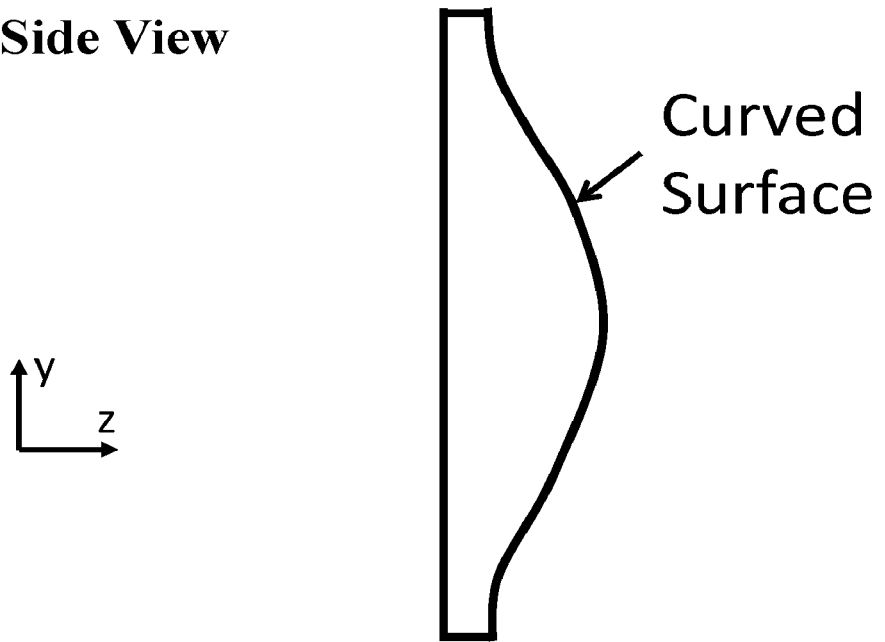
FIG. 5B illustrates, in accordance with various embodiments of the disclosure, that an aspherical lens has at least one curved surface with an aspherical shape defined by an equation.

In some embodiments, a spherical lens is used as the collecting lens to collect the fluorescence and the scattered light with a forward angle from the sample flow. The spherical lens has at least one curved surface that has a spherical shape, as shown in FIG. 5A. In some embodiments, an aspherical lens is used as the collecting lens to collect the fluorescence and the scattered light with a forward angle. An aspherical lens is advantageous to increase the collection efficiency of the fluorescence from the sample flow. The aspherical lens, as shown in FIG. 5B, has at least one curved surface with an aspherical shape defined by the following equation.

$$X = \frac{C_0 \cdot Y^2}{1 + \sqrt{1 - (K+1) \cdot C_0^2 \cdot Y^2}} + \sum_{i=1}^{n} C_i Y^i$$

In the above equation: X represents position in the optical axis direction; Y represents distance from the lens center in the direction in which the optical axis advances; K represents shape coefficient; $C_0$ represents coefficient representing the curvature of the based surface (spherical surface basis of the aspherical surface); C represents aspherical surface coefficient; and i represents an integer (1 to n).

Figure 6A:
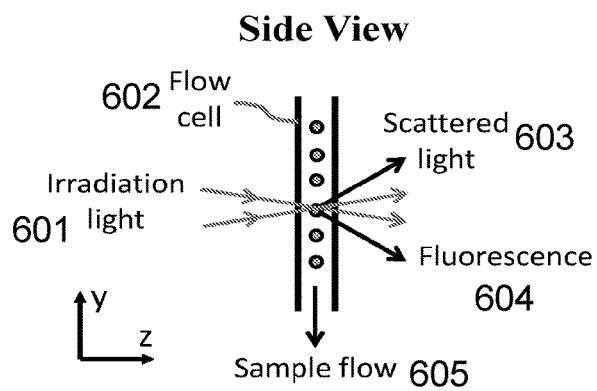
FIGS. 6A and 6B illustrate, in accordance with various embodiments of the disclosure, that the flow cell can be positioned at or close to the focal point of the one lens (FIG. 6A) and away from the focal point of another lens (FIG. 6B).
Figure 6B:
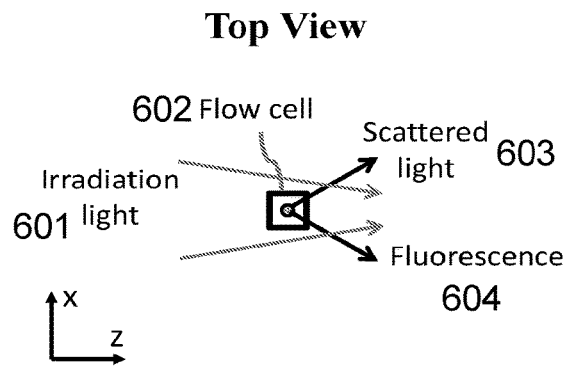
Figure 6C:
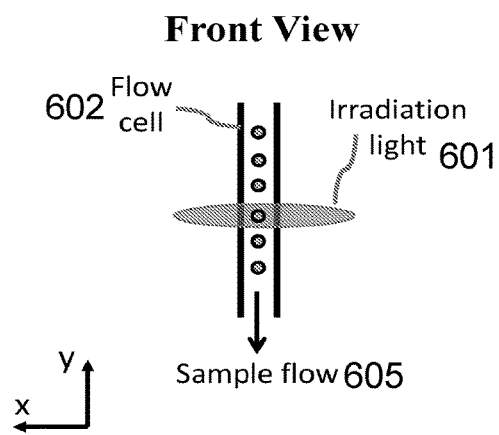
FIGS. 6C and 6D illustrate, in accordance with various embodiments of the disclosure, that the diameter ($d_1$) of the elliptical beam spot along the sample flow's direction (i.e., the diameter along the y-axis) is narrow and that the diameter ($d_2$) of the elliptical beam spot perpendicular to the sample flow's direction (i.e., the diameter along the x-axis) is wide.
Figure 6D:
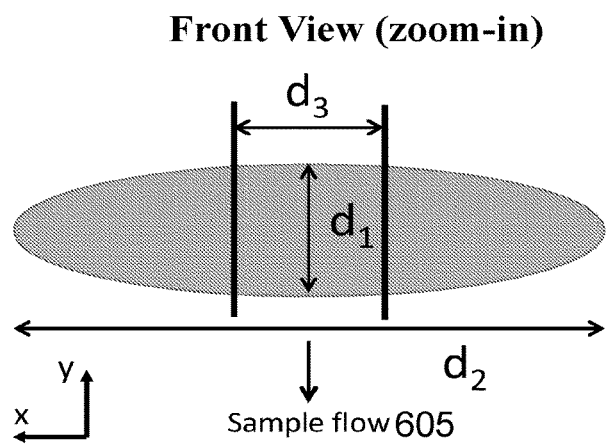

In the detection unit of FIG. 2A and FIG. 2B, an elliptical beam spot is used to irradiate the sample flow in the flow cell. This elliptical beam spot is achieved by using the two cylindrical lenses 210 and 211. The two cylindrical lenses are positioned in such an orientation that their cylinder axes are perpendicular to each other. The flow cell is positioned at or close to the focal point of the lens 211, as shown in FIG. 6A. Therefore, the diameter ($d_1$) of the elliptical beam spot along the sample flow's direction is narrow, i.e., the diameter along the y-axis as shown in FIG. 6C and FIG. 6D. Meanwhile, the flow cell is positioned away from the focal point of the lens 210, as shown in FIG. 6B. Therefore, the diameter ($d_2$) of the elliptical beam spot perpendicular to the sample flow's direction is wide, i.e., the diameter along the x-axis as shown in FIG. 6C and FIG. 6D. The aspect ratio R of the elliptical beam spot is defined as follows.

$R = d_2/d_1$

An elliptical beam spot has an aspect ratio R>1. When R=1, the beam spot becomes a circular shape. The sample flow width irradiated under the beam spot, as shown in FIG. 6D, is denoted as $d_3$. One advantage of using an elliptical beam spot is that the two diameters, $d_1$ and $d_2$, could be optimized separately. In various embodiments, $d_1$ and $d_2$ can be adjusted in a device or device system as described herein by adjusting the focusing module configuration, for example, adjusting the positions of the light source, the two cylindrical lenses 210 and 211, and the flow cell, or changing these components.

For example, the diameter $d_1$ can be optimized for measuring cells of different sizes. To fully irradiate the cells with the beam spot, the diameter $d_1$ has to be larger than the diameter of the target cells. To reduce the background being irradiated by the beam spot, however, the diameter $d_1$ should be as small as possible. Therefore, the diameter $d_1$ is often chosen to be close to or slightly larger than the diameters of the target cells. This is helpful to increase the amplitude of the fluorescence from the measurement sample and to improve the signal-to-noise ratio of the fluorescence from the target cells.

In some embodiments, a $d_1$ of about 4-7 μm is used for measuring cells with a diameter of about 1-3 μm. In some embodiments, a $d_1$ of about 7-10 μm is used for measuring cells with a diameter of about 1-6 μm. In some embodiments, a $d_1$ of about 10-20 μm is used for measuring cells with a diameter of about 1-9 μm. In some embodiments, a $d_1$ of about 20-30 μm is used for measuring cells with a diameter of about 1-19 μm. In some embodiments, a $d_1$ of about 30-50 μm is used for measuring cells with a diameter of about 1-29 μm. In some embodiments, a $d_1$ of about 50-80 μm is used for measuring cells with a diameter of about 1-49 μm. In some embodiments, a $d_1$ of about 80-99 μm is used for measuring cells with a diameter of about 1-79 μm.

Figure 7A:
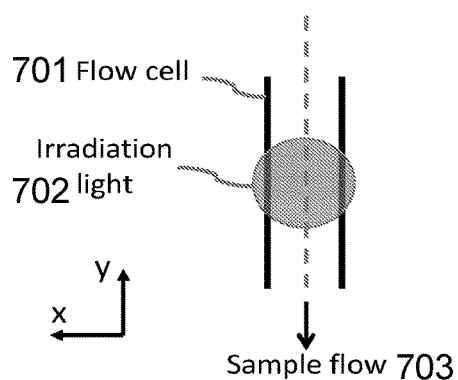
FIG. 7A illustrates, in accordance with various embodiments of the disclosure, a non-limiting example where a circular beam spot is used to irradiate the sample flow.
Figure 7B:
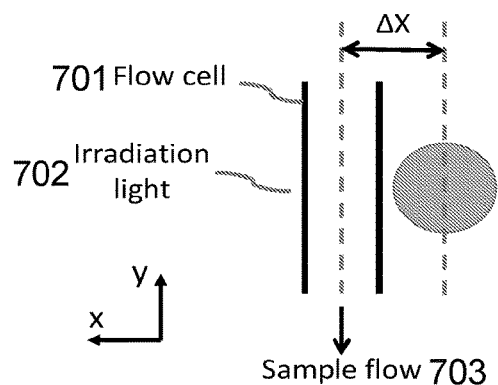
FIG. 7B illustrates, in accordance with various embodiments of the disclosure, that when the beam spot and the sample flow have an alignment deviation $\Delta X$, the beam spot can no longer irradiate the sample flow.

For another example, the diameter $d_2$ can be optimized for alignment between the sample flow and the irradiation light in the beam spot. Some traditional analyzers use a circular beam spot to irradiate the sample flow, such as the one disclosed in US Patent Application Publication No. 2015/0309049 A1. A circular beam spot has an aspect ratio of R=1 (i.e., $d_2$=$d_1$). After $d_1$ is chosen for cell sizes, the circular beam spot limits the option of $d_2$. FIG. 7A shows a non-limiting example where a circular beam spot is used to irradiate the sample flow. When the beam spot and the sample flow have an alignment deviation ΔX, as shown in FIG. 7B, the beam spot is no longer able to irradiate the sample flow. For example, when the beam spot has a $d_1$ of 20 μm, the circular beam spot limits $d_2$ to be equal to $d_1$. For a sample flow width $d_3$ of 20 μm, an alignment deviation of 20 μm would cause the beam spot not to irradiate the sample flow.

Figure 7C:
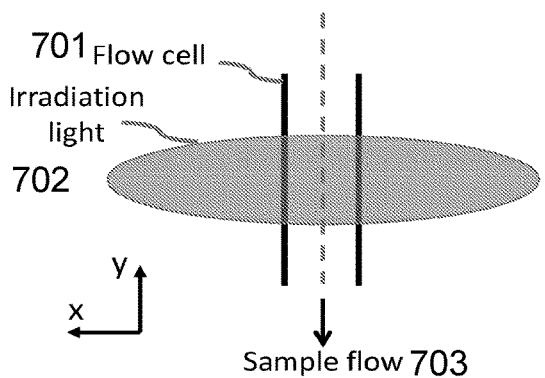
FIG. 7C illustrates, in accordance with various embodiments of the disclosure, a non-limiting example where an elliptical beam spot is used to irradiate the sample flow.
Figure 7D:
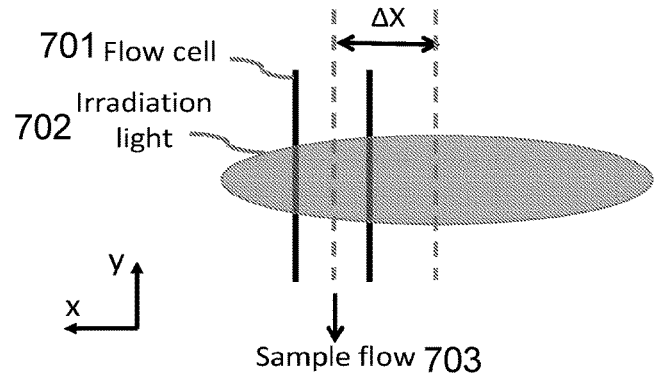
FIG. 7D illustrates, in accordance with various embodiments of the disclosure, that with the same alignment deviation $\Delta X$, the beam spot can still irradiate the sample flow.

On the contrary, in an elliptical beam spot, the two diameters, $d_1$ and $d_2$, could be optimized separately. The elliptical beam spot has an aspect ratio of R>1 (i.e., $d_2$>$d_1$). FIG. 7C shows a non-limiting example where an elliptical beam spot is used to irradiate the sample flow. With the same amount of alignment deviation ΔX, as shown in FIG. 7D, the beam spot can still irradiate the sample flow. For example, when the beam spot has a $d_1$ of 20 μm, the elliptical beam spot can still have a d larger than e.g., 200 μm. For a sample flow width d of 20 μm, the beam spot can still irradiate the sample flow even with an alignment deviation of 20 μm. The tolerance of alignment deviation between the flow cell and the beam spot is particularly important for applications where the flow cell is replaceable or disposable after measurement. Furthermore, an irradiation light with a Gaussian beam profile is often used in cytometer analysis, and a wide $d_2$ also helps to improve the irradiation light's uniformity along the sample flow width.

In some embodiments, a $d_2$ of about 40-500 μm is used for irradiating a flow cell with a sample flow width of about 4-10 μm. In some embodiments, a $d_2$ of about 100-1,000 μm is used for irradiating a flow cell with a sample flow width of about 10-20 μm. In some embodiments, a $d_2$ of about 200-1,500 μm is used for irradiating a flow cell with a sample flow width of about 20-30 μm. In some embodiments, a $d_2$ of about 300-2,000 μm is used for irradiating a flow cell with a sample flow width of about 30-40 μm. In some embodiments, a $d_2$ of about 400-2,500 μm is used for irradiating a flow cell with a sample flow width of about 40-50 μm. In some embodiments, a $d_2$ of about 500-5,000 μm is used for irradiating a flow cell with a sample flow width of about 50-100 μm.

Figure 8:
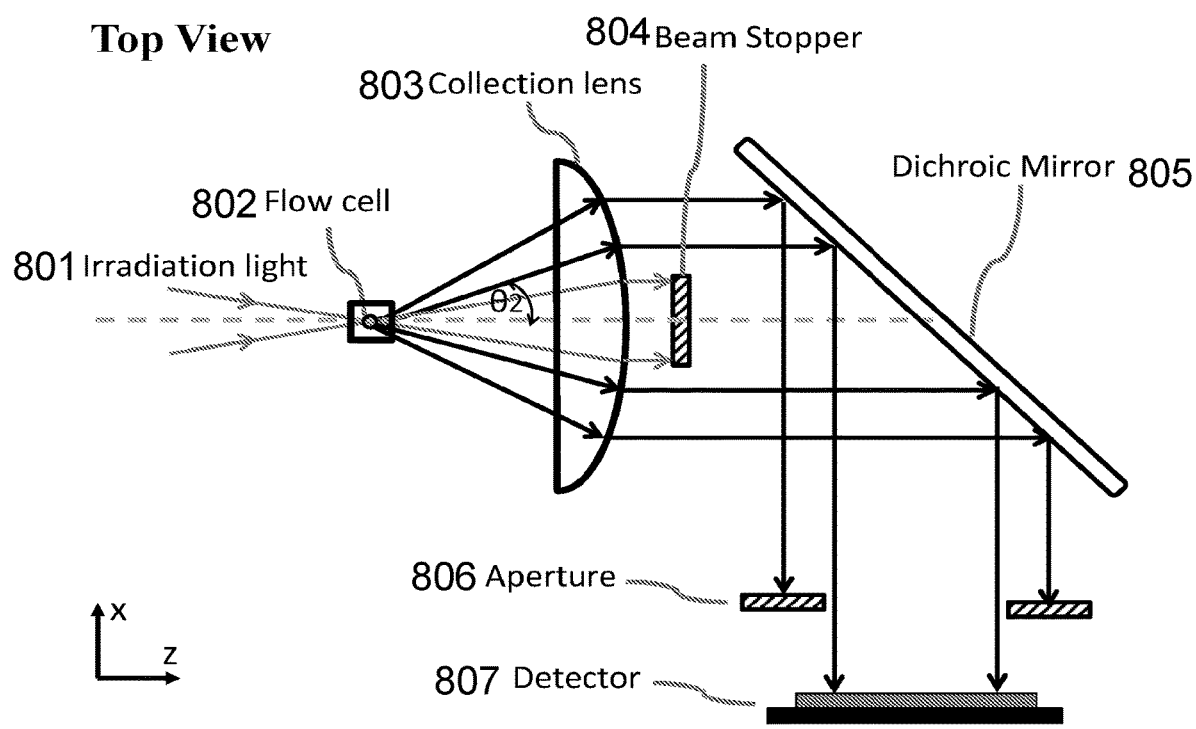
FIG. 8 illustrates, in accordance with various embodiments of the disclosure, a zoom-in view of the detection unit from FIG. 2B.

In the example of FIG. 2A and FIG. 2B, the aperture 214 is used to block light outside the transparent opening of the aperture from entering the detector 207. By positioning the transparent opening of the aperture 214 at the center the detector 207 and by adjusting the size of the opening, the aperture can be used to block scattered light with a scattering angle more than a threshold angle $\theta_2$, as shown in FIG. 8, which is a zoom-in view of the detection unit from FIG. 2B.

In the example of FIG. 2A and FIG. 2B, the elliptical beam spot is obtained by focusing the light emitted from the light source with a focusing module 203 that comprises two cylindrical lenses 210 and 211. In other embodiments, the elliptical beam spot can be obtained by using other focusing module configurations, which include but are not limited to modules with only one cylindrical lens, modules with no cylindrical lens, modules with an anamorphic prism pair (e.g., U.S. Pat. No. 5,596,456, which is incorporated herein by reference in its entirety as if fully set forth), modules with a diffraction grating component, and modules with other beam-shaping optics (e.g., U.S. Pat. No. 6,975,458, which is incorporated herein by reference in its entirety as if fully set forth), etc.

Figure 9A:
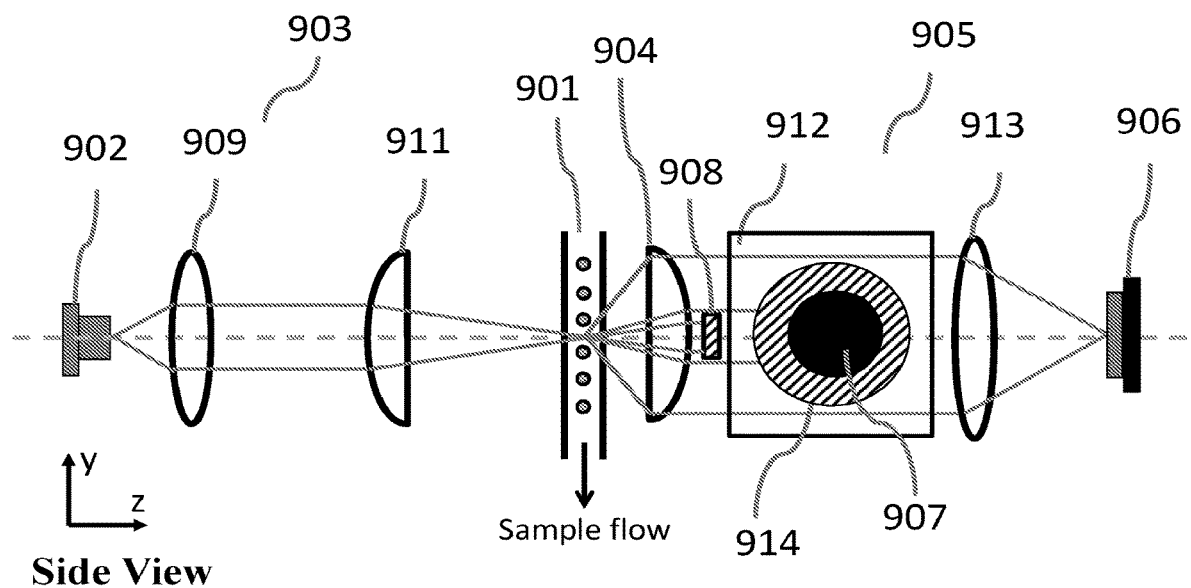
FIGS. 9A and 9B illustrate, in accordance with various embodiments of the disclosure, another non-limiting example to obtain the elliptical beam spot, where the focusing module 903 comprises a condenser lens 909 and one cylindrical lens 911.
Figure 9B:
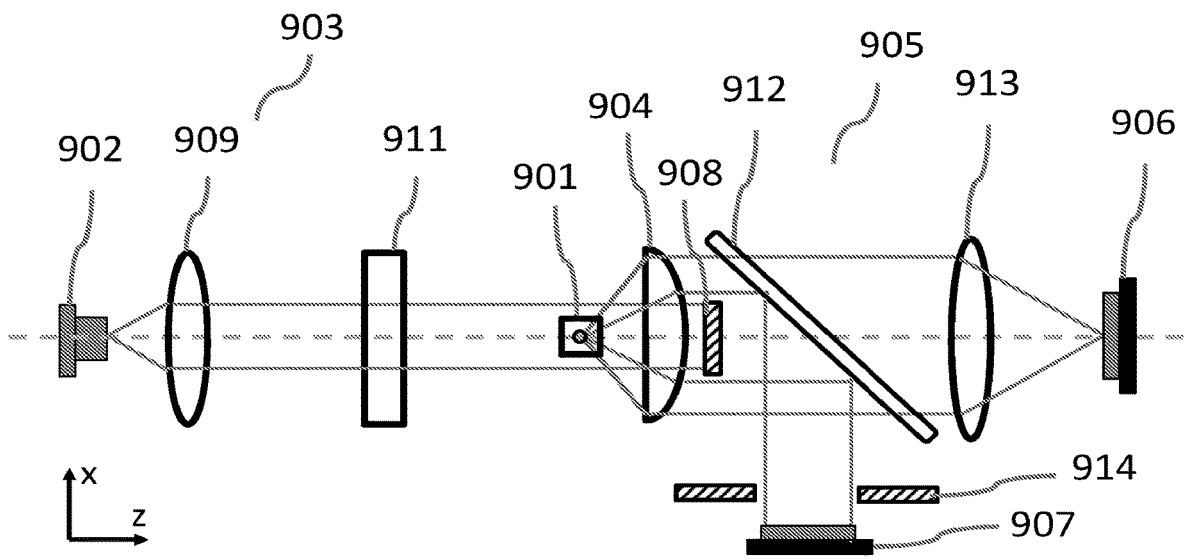

FIG. 9A (side view) and FIG. 9B (top view) shows another non-limiting example to obtain the elliptical beam spot, where the focusing module 903 comprises a condenser lens 909 and a cylindrical lens 911. The light emitted from the light source 902 is collimated into parallel light with the condenser lens 909, and further passes through the cylindrical lens 911. Along the cylinder axis of lens 911, the light beam is focused by the curved surface of the cylindrical lens (i.e., focused along the y-axis here). Perpendicular to the cylinder axis of lens 911, the light beam is not focused and remains parallel. By positioning the flow cell at or close to the focal point of the cylindrical lens 901, the irradiation light forms an elliptical beam spot on the sample flow. In various embodiments, $d_1$ and $d_2$ can be adjusted in a device or device system as described herein by adjusting the focusing module configuration, for example, adjusting the positions of the light source, the condenser lens 909, the cylindrical lens 911, and the flow cell, or changing these components.

In this example, a collecting lens 904 is used to collect both the fluorescence and the scattered light with a forward angle from the sample flow. A beam stopper 908 is positioned behind the collecting lens to block the irradiation light from entering the receiving module 905. The receiving module 905 comprises a dichroic mirror 912, which separates the scattered light with a forward angle and the fluorescence into two optical paths. A condenser lens 913 condenses the fluorescence passing through the dichroic mirror into the detector 906. An aperture 914 in front of the detector 907 limits the scattered light receivable at the detector 907.

Figure 10A:
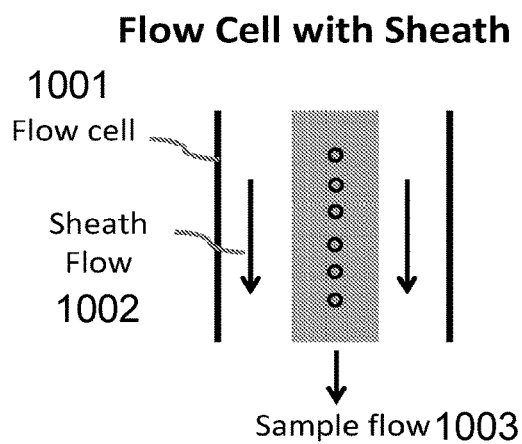
FIG. 10A illustrates, in accordance with various embodiments of the disclosure, a flow cell with sheath flow can be used, where the sample flow is surrounded by a sheath flow in the flow cell.
Figure 10B:
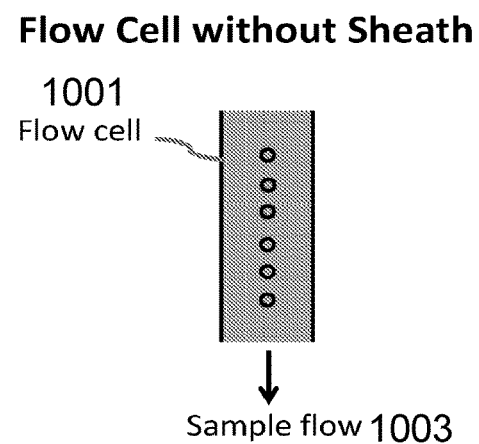
FIG. 10B illustrates, in accordance with various embodiments of the disclosure, a flow cell without sheath flow can be used, where there is no sheath flow surrounding the sample flow in the flow cell.

The detection unit can use any types of flow cell design, including but not limited to a flow cell with sheath flow, a sheathless flow cell, etc. In some embodiments, a flow cell with sheath flow can be used, where the sample flow is surrounded by a sheath flow in the flow cell, as shown in FIG. 10A. The sheath flow 1002 focuses the sample flow 1003 into a stream that has a width smaller than the inner width of the flow cell 1001 in the direction perpendicular to the sample flow 1003. In some embodiments, a flow cell 1001 without sheath flow 1002 can be used, as shown in FIG. 10B. In this sheathless flow cell design, the sample flow 1003 is confined by the physical geometry of the flow cell, and has a width that is equal to the inner width of the flow cell 1001 in the direction perpendicular to the sample flow 1003. In certain embodiments, the detection unit uses a sheathless flow cell. Examples of the sheathless flow cell include but are not limited to those disclosed in U.S. Patent Application No. 62/497,075, U.S. patent application Ser. No. 15/803,133, and U.S. patent application Ser. No. 15/819,416, which are incorporated herein by reference in their entirety as if fully set forth.

Figure 11:
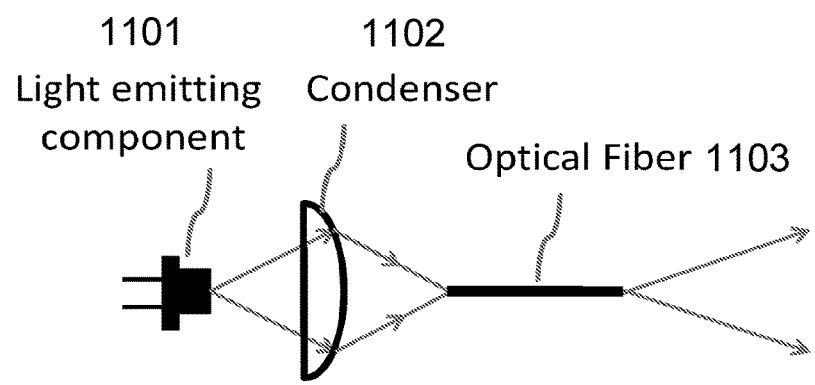
FIG. 11 illustrates, in accordance with various embodiments of the disclosure, a non-limiting example of the light source, which comprises a light-emitting component, an optical fiber, and a condenser lens.

The detection unit can use any types of light source to provide the irradiation light illuminating the sample flow, including but not limited to a laser module, a laser diode, a LED device, a halogen lamp, etc. In some embodiments, as shown in FIG. 11, the light source comprises a light-emitting component 1101, an optical fiber 1103, and a condenser lens 1102. The light-emitting component emits light, which is focused by the condenser lens into one end of the optical fiber. The light exiting from the other end of the fiber is used to irradiate the sample flow. In certain embodiments, the optical fiber is a single-mode fiber. It can be advantageous to use a single-mode fiber. For example, when a multi-mode light enters the single-mode fiber, some components of the light are removed by the fiber and the light existing from the optical fiber becomes single-mode (e.g., the fundamental Gaussian mode). In certain embodiments, the light-emitting component is a laser diode, a LED device, or a halogen lamp.

The detection unit of the flow cytometer can use any types of light detectors to measure the fluorescence and the scattered light signals, including but not limited to bipolar phototransistor, photosensitive field-effect transistor, photomultiplier tubes (PMT), avalanche photodiode (APD), photodiode, CCD device, CMOS device, and silicon photomultipliers (SiPM), etc. In some embodiments, the detection unit measures the intensity of the light signal. In some embodiments, the detection unit measures the time duration of the light signal. In some embodiments, the detection unit measures the space distribution of the light signal. In some embodiments, the detection unit measures the image information of the light signal.

In various embodiments, a signal analysis unit is used to analyze signals measured by detectors in the detection unit. In some embodiments, the signal analysis unit analyzes the signal of the scattered light and the signal of the fluorescent light from the detection unit for measurement of particles and/or cells in the sample flow.

In various embodiment, the flow cell is part of a cartridge device. Non-limiting examples of a cartridge device with a flow cell are shown in U.S. patent application Ser. No. 15/803,133 and U.S. patent application Ser. No. 15/819,416, which are incorporated herein by reference in their entirety as if fully set forth. In various embodiment, the cartridge device is placed in an analyzer device comprising a light source, a collecting lens and a detector to perform measurement of particles and/or cells in a sample flow in the flow cell. In various embodiment, the cartridge device is removed from the analyzer device after the measurement is completed. In some embodiments, the cartridge device receives a sample with particles and/or cells and further prepares a measurement sample from the sample with particles and/or cells and a reagent, and then provides the measurement sample to the flow cell to form a sample flow for the measurements.

A device or device system as described herein can be used for analyzing any types of samples containing cells. It can also be used for analyzing any types of samples containing particles, including but not limited to liquid droplets, molecules (e.g., nucleic acid molecules, protein molecules, etc.), viruses, beads, nanoparticles, etc. Its sample supply unit provides to its detection unit a measurement sample containing cells, particles, or both. Its detection unit detects various signals from the cells, particles, or both in the measurement sample. Its analysis unit analyzes the detected signals (e.g., scattered light with a forward angle, fluorescence, or both) to obtain information of the measurement sample (e.g., cell count, intrinsic fluorescence of individual cells, fluorescence of individual cells labeled with fluorophore, etc.). Based on the detected signals, the analysis unit can further obtain additional information of the measurement sample, for example, classifying cells into different types, characterizing individual cells, characterizing cell populations in the measurement sample, etc.

In some embodiments, a device or device system as described herein is used for analyzing cells in blood samples (e.g., blood samples from human or other species such as canine, feline, equine, bovine, ferret, gerbil, rabbit, pig, mini pig, and guinea pig, etc.). As a non-limiting example, the device or device system can be used to analyze human blood samples, so as to detect and classify the cells in a human blood sample into three major types including white blood cells, red blood cells and platelet cells. The device or device system can further be used to classify white blood cells into five major subtypes including the lymphocytes, monocytes, neutrophils, eosinophils, and basophils. The device or device system can further be used to detect the existence and level of antigen expressions on cells, and use the antigen expression levels to classify cells into different types. For a non-limiting example, the device or device system can be used to classify lymphocyte cells into T-Cells, NK-Cells, $CD4^+$ cells, $CD8^+$ cells, etc. The device or device system can be used to further detect and classify other cells in human blood samples, for example, those cells described in US Patent Application Publication No. 2014/0170680 A1, which is incorporated herein by reference in its entirety as if fully set forth.

For any specific type of biological samples for measurement, the cells in the sample have known size ranges. Therefore, the size of the sample flow in the flow cell and the diameters of the elliptical beam spot can be optimized accordingly in the detection unit. For example, cells in a human blood sample can be analyzed. Human blood cells have known size ranges, for example, about 1-3 μm in diameter for platelet cells, about 6-8 μm in diameter for red blood cells, and about 7-15 μm in diameter for white blood cells. Accordingly, the detection unit can use a sample flow having $d_3$ of about 20-50 μm, and an elliptical beam spot having $d_1$ of about 16-50 μm and $d_2$ of about 160-2,500 μm.

In some embodiments, a device or device system as described herein is used to analyze the white blood cells in a blood sample. In some embodiments, the sample supply unit prepares a measurement sample by mixing the blood sample with a staining reagent containing at least a fluorescent labelling compound, which includes but is not limited to fluorophore-conjugated antibodies, fluorescent-particles-conjugated antibodies, and fluorescent dyes, etc. The fluorescent labelling compound labels the white blood cells with high affinity.

In some embodiments, the sample supply unit prepares a measurement sample by mixing the blood sample with a staining reagent containing at least a fluorescent dye. This fluorescent dye can be a nucleic acid dye. Examples of the fluorescent dye include but are not limited to propidium iodide, ethidium bromide, DAPI, Hoechst dyes, Acridine Orange, 7-AAD, LDS 751, TOTO families of dyes, TO-PRO families of dyes, SYTO family of dyes, Thiazole Orange, Basic Orange 21, Auramine-O, and the dye compounds disclosed in U.S. Pat. No. 6,004,816, etc., which is incorporated herein by reference in its entirety as if fully set forth. The fluorescent dye labels the nucleic acids of the white blood cells with high affinity.

The prepared measurement sample is supplied to the flow cell of the detection unit to form a sample flow. The sample flow is illuminated with an irradiation light, and the signals (e.g., fluorescence and scattered light with the forward angle) from the sample flow are measured by the two detectors in the detection unit. The analysis unit analyzes the detected signals (e.g., intensities of the fluorescence and scattered light) to obtain the information of the measurement sample, which includes but is not limited to one or more of the following parameters: the total count of the white blood cells, and the counts and percentages of different subtypes of the white blood cell (e.g., lymphocytes, monocytes, neutrophils, eosinophils and basophils, etc.).

In some embodiments, the staining reagent further comprises a lysing compound, which lyses red blood cells in the blood sample. Because the concentration of red blood cell is usually higher than the concentration of white blood cells, it helps to improve the detection of the signals from white blood cells in the sample flow. Examples of the lysing compound include but are not limited to ammonium salts, quaternary ammonium salts, pyridinium salts, hydroxylamine salts, nonionic surfactants, ionic surfactants, dodecyl sodium sulfate (SDS), sodium lauryl sulfate (SLS), and their combinations, and any other known erythrocyte lysing compounds.

Figure 12:
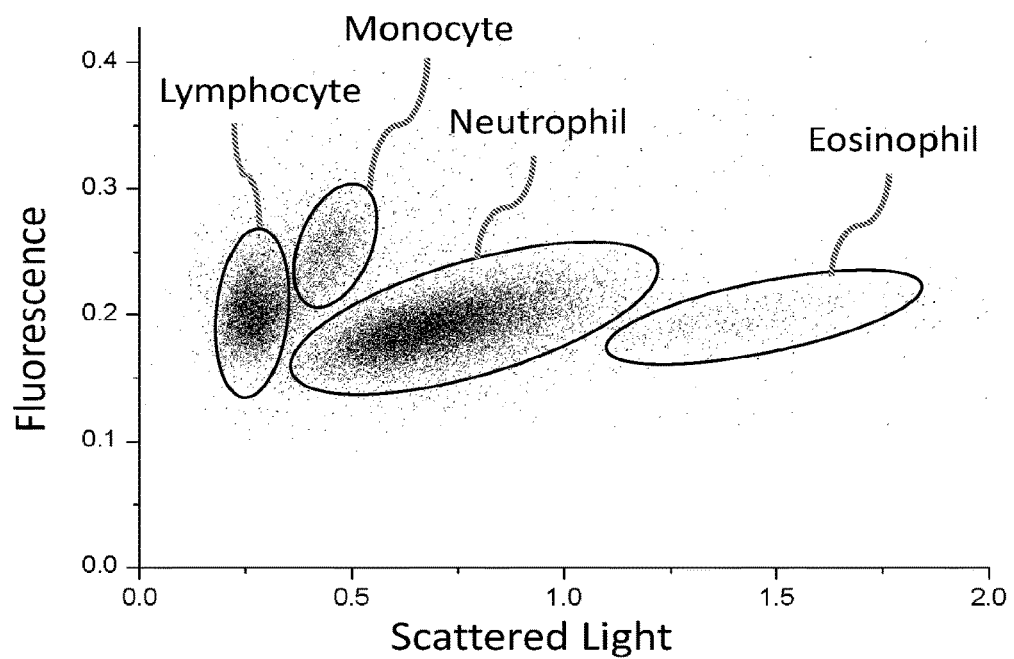
FIG. 12 illustrates, in accordance with various embodiments of the disclosure, one non-limiting example of a scatter plot of fluorescence and scattered light, in which each dot represents one white blood cell being detected in the sample flow.

In a non-limiting example, the fluorescent dye in the staining reagent is Thiazole Orange. A dichroic mirror has a long-pass threshold wavelength of 560 nm is used to separate the fluorescence signal from the collected light. An obstruction bar is used as the beam stopper to block the irradiation light. The obstruction bar has a bar width that blocks the scattered light with a scattering angle $\theta_1$ less than about 4 degrees. An aperture having a transparent opening is used in front of the detector that receives the light comprising the scattered light, and the aperture blocks the scattered light with a scattering angle $\theta_2$ more than about 12 degrees from entering the detector. The analysis unit uses the detected signals of fluorescence and scattered light to produce a scatter plot. In one non-limiting example of the scatter plot, as shown in FIG. 12, each dot represents one white blood cell being detected in the sample flow. The analysis unit enumerates the total number of dots in the scatter plot to determine the total count of the white blood cells in the blood sample. Furthermore, the dots in the scatter plot fall into distinguished clusters. The analysis unit enumerates the number of dots in each cluster to determine the counts and percentages of different subtypes of the white blood cell including lymphocytes, monocytes, neutrophils, and eosinophils.

Figure 13:
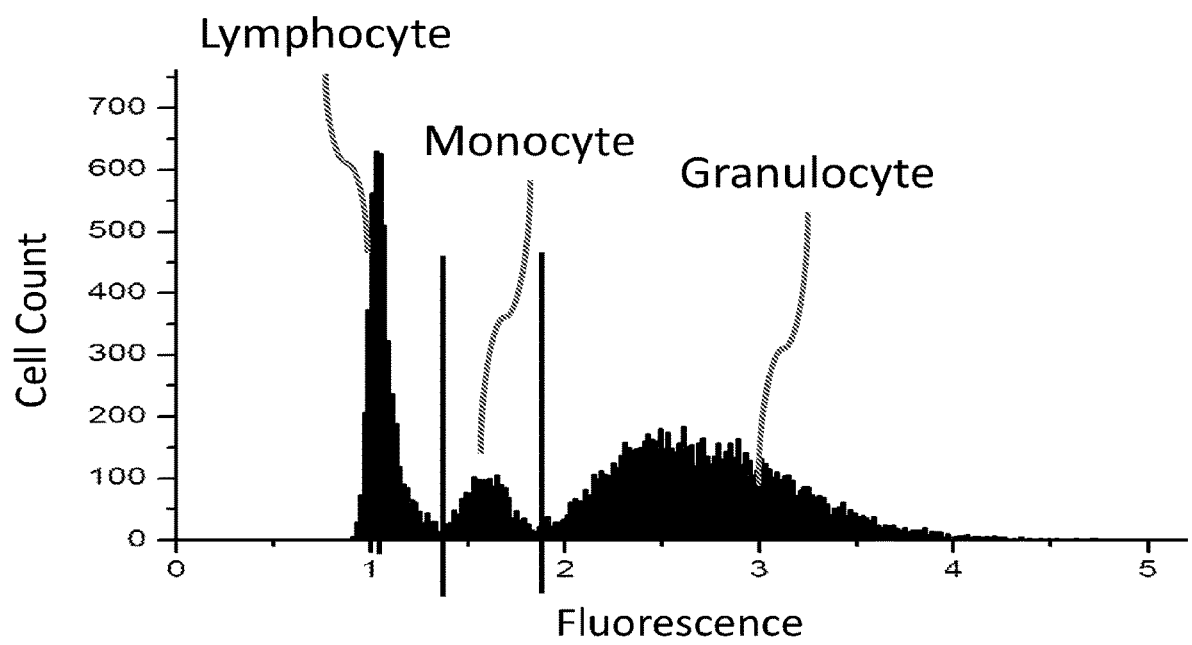
FIG. 13 illustrates, in accordance with various embodiments of the disclosure, one non-limiting example of a histogram plot, in which the fluorescence intensities are plotted as the x-axis, and the numbers of the detected cells with the corresponding fluorescence intensities are plotted as the y-axis.

In another non-limiting example, the fluorescent dye in the staining reagent is Acridine Orange. A dichroic mirror has a long-pass threshold wavelength of 610 nm is used to separate the fluorescence signal from the collected light. The analysis unit uses the detected signals of fluorescence to produce a histogram plot. In one non-limiting example of the histogram plot, as shown in FIG. 13, the fluorescence intensities are plotted as the x-axis, whereas the numbers of the detected cells with the corresponding fluorescence intensities are plotted as the y-axis. The histogram indicates three distinguished peaks. The peak with the low fluorescence intensities corresponds to lymphocyte cells; the peak with the middle fluorescence intensities corresponds to monocyte cells; and the peak with high fluorescence intensities corresponds granulocyte cells, which include the neutrophil cells, eosinophil cells and basophil cells. The analysis unit enumerates the number of cells in all the peaks to determine the total count of the white blood cells, and further enumerates the number of cells in each peak to determine the counts and percentages of lymphocyte cells, monocyte cells and granulocyte cells.

In some embodiments, a device or device system as described herein is used to analyze the red blood cells and platelets in a blood sample. In some embodiments, the sample supply unit prepares a measurement sample by mixing the blood sample with a staining reagent containing at least a fluorescent labelling compound, which includes but is not limited to fluorophore-conjugated antibodies, fluorescent-particle-conjugated antibodies, and fluorescent dyes, etc. The fluorescent labelling compound labels the red blood cells and platelets with high affinity.

In some embodiments, the sample supply unit prepares a measurement sample by mixing the blood sample with a staining reagent containing at least a fluorescent dye. This fluorescent dye can be a nucleic acid dye. Examples of the fluorescent dye include but are not limited to propidium iodide, ethidium bromide, DAPI, Hoechst dyes, Acridine Orange, 7-AAD, LDS 751, TOTO families of dyes, TO-PRO families of dyes, SYTO family of dyes, Thiazole Orange, Basic Orange 21, Auramine-O, and the dye compounds disclosed in U.S. Pat. No. 6,004,816, etc., which is incorporated herein by reference in its entirety as if fully set forth. The fluorescent dye labels the nucleic acids in the red blood cells and platelets with high affinity.

The prepared measurement sample is supplied to the flow cell of the detection unit to form a sample flow. The sample flow is illuminated with an irradiation light, and the signals (e.g., fluorescence and scattered light with the forward angle) from the sample flow are measured by the two detectors in the detection unit. The analysis unit analyzes the detected signals (e.g., intensities of the fluorescence and scattered light) to obtain the information of the measurement sample, which includes but is not limited to one or more of the following parameters: the total count of the red blood cells, the total count of the platelets, the sizes of individual red blood cells, the size distribution of the red blood cell population, the sizes of individual platelets, and the size distribution of the platelet population, the count of reticulocyte cells, and the count of immature platelet cells, etc.

In some embodiments, the staining reagent further comprises a sphering compound. The sphering compound is used to transform the red blood cells in the prepared sample from a disk shape into a spherical shape. With a spherical shape, the intensities of the scattered light from individual red blood cells become independent of the cells' orientation in the flow cell. Examples of the sphering compound include but are not limited to surfactants such as sodium dodecyl sulfate (SDS) and sodium lauryl sulfate (SLS), etc.

Figure 14:
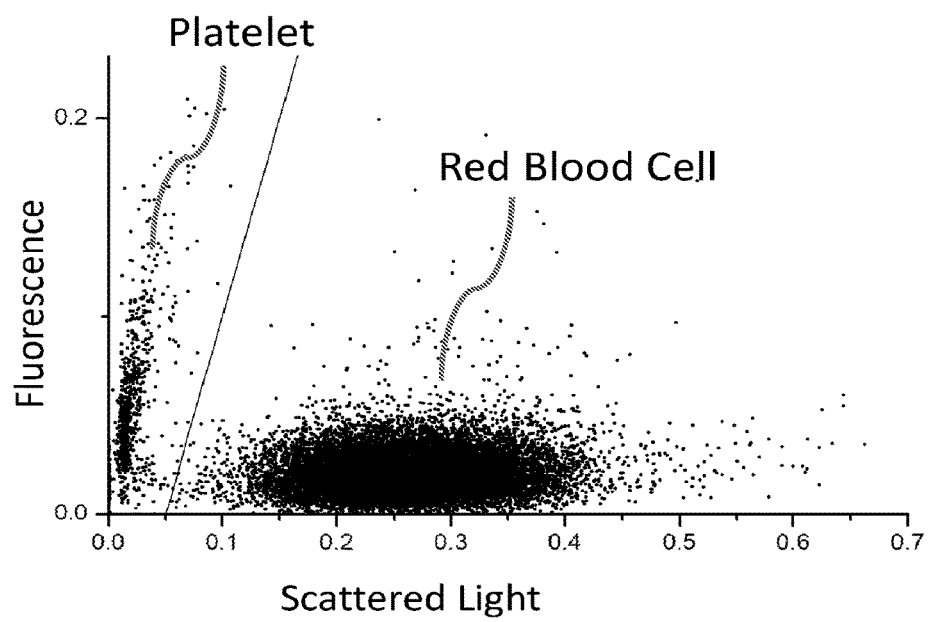
FIG. 14 illustrates, in accordance with various embodiments of the disclosure, one non-limiting example of a scattered plot of fluorescence and scattered light, in which each dot represents one red blood cell or platelet being detected in the sample flow.

In a non-limiting example, the fluorescent dye used in the staining reagent is Acridine Orange. A dichroic mirror has a long-pass threshold wavelength of 590 nm is used to separate the fluorescence signal from the collected light. An obstruction bar is used as the beam stopper to block the irradiation light. The obstruction bar has a bar width that blocks the scattered light with a scattering angle $\theta_1$ less than about 1 degree. An aperture having a transparent opening is used in front of the detector that receives the light comprising the scattered light, and the aperture blocks the scattered light with a scattering angle $\theta_2$ more than about 5 degrees from entering the detector. The analysis unit uses the detected signals of fluorescence and scattered light to produce a scatter plot. In one non-limiting example of the scattered plot, as shown in FIG. 14, each dot represents one cell being detected in the sample flow. The dots in the scatter plot fall into two distinguished clusters. The cluster with lower scattered light intensities and higher fluorescence intensities correspond to platelets, whereas the cluster with higher scattered light intensities and lower fluorescence intensities correspond to red blood cells. The analysis unit enumerates the number of dots in each cluster to determine the total count of platelets and the total count of red blood cells. The analysis unit can evaluate the intensities of the scattered light of all dots in the red blood cell cluster to determine the sizes of individual red blood cells and the size distribution of the red blood cell population in the measurement sample. The analysis unit can also evaluate the intensities of the scattered light of all dots in the platelet cluster to determine the sizes of individual platelets and the size distribution of the platelet population in the measurement sample.

In some embodiments, a device or device system as described herein is used to analyze the red blood cells and platelets in a blood sample. The sample supply unit prepares a measurement sample by mixing the blood sample with a dilution reagent containing at least one compound that adjusts the osmolality of the prepared sample. The reagent is used to dilute the concentration of the red blood cells in the prepared sample, while minimizing the undesirable lysing of the red blood cells. Examples of the osmolarity-adjusting compound include but are not limited to: salts containing cations (e.g., $Na^+$, $K^+$, $NH_4^+$, $Ca^{2+}$, and $Mg^{2+}$ containing salts); salts containing anions (e.g., $Cl^-$, $Br^-$, $NO_3^-$, $CO_3^{2-}$; $HCO_3^-$, $SO_4^{2-}$, $HSO_4^-$, $PO_4^{3-}$, $HPO_4^{2-}$, $H_2PO_4^-$, $COOH^-$, and $CH_3COO^-$); organic compounds such as sugars (e.g., glucose and sucrose); and alcohols (e.g., ethanol and methanol), etc. The prepared measurement sample is supplied to the flow cell of the detection unit to form a sample flow. The sample flow is illuminated with an irradiation light, and the signals of the scattered light with the forward angle are measured in a detector. The analysis unit analyzes the detected signals to obtain information of the measurement sample, which includes but is not limited to one or more of the following parameters: the total count of the red blood cells, the total count of the platelets, the sizes of individual red blood cells, the size distribution of the red blood cell population, the sizes of individual platelets, and the size distribution of the platelet population, the count of reticulocyte cells, and the count of immature platelet cells, etc.

Figure 15:
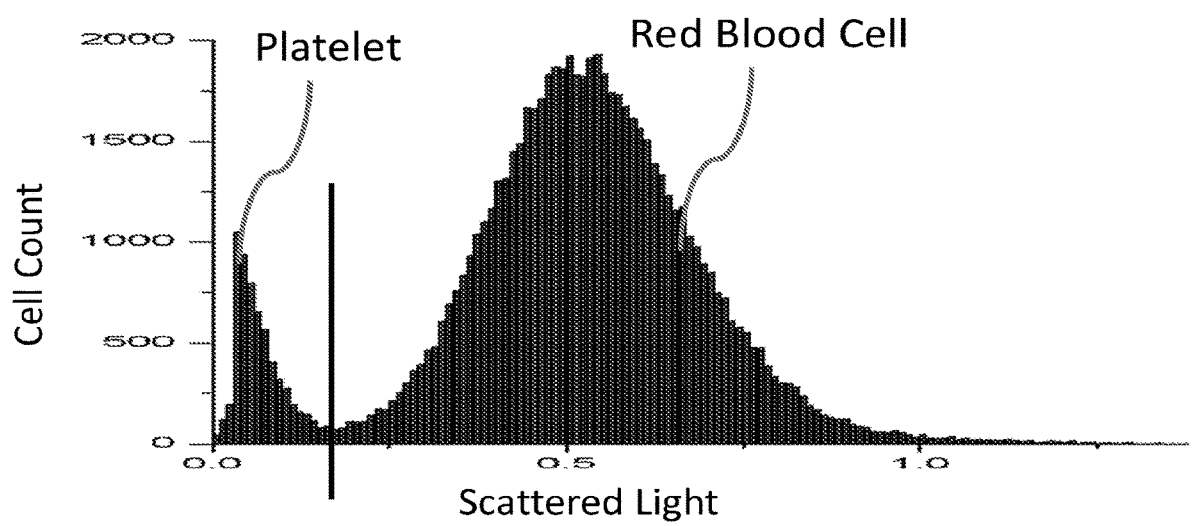
FIG. 15 illustrates, in accordance with various embodiments of the disclosure, one non-limiting example of a histogram plot, in which the intensities of the scattered light are plotted as the x-axis, and the numbers of the detected cells with the corresponding intensities of the scattered light are plotted as the y-axis

In a non-limiting example, the osmolarity-adjusting compound in the dilution reagent is sodium chloride. In this example, a dichroic mirror may not be required. An obstruction bar is used as the beam stopper to block the irradiation light. The obstruction bar has a bar width that blocks the scattered light with a scattering angle $\theta_1$ less than about 1 degree. An aperture having a transparent opening is used in front of the detector that receives the light comprising the scattered light, and the aperture blocks the scattered light with a scattering angle $\theta_2$ more than about 7 degrees from entering the detector. The analysis unit uses the detected signals of the scattered light to produce a histogram plot, as shown in FIG. 15. In this histogram plot, the intensities of the scattered light are plotted as the x-axis, and the numbers of the detected cells with the corresponding intensities of the scattered light are plotted as the y-axis. The histogram indicates two distinguished peaks. The peak with the lower intensities corresponds to platelets, and the peak with higher intensities corresponds to red blood cells. The analysis unit enumerates the number of cells in each peak to determine the total count of platelets and the total count of red blood cells. The analysis unit can evaluate the scattered light intensities from the cells in the red blood cell peak to determine the sizes of individual red blood cells and the size distribution of the red blood cell population in the sample. The analysis unit can also evaluate the scattered light intensities from the cells in the platelet peak to determine the sizes of individual platelets and the size distribution of the platelet population in the measurement sample.

In some embodiments, a device or device system as described herein is used to analyze the white blood cells, red blood cells and platelets in a blood sample. The sample supply unit prepares one measurement sample by mixing one portion of the blood sample with a first staining reagent containing at least a first fluorescent dye. Also, the sample supply unit prepares another measurement sample by mixing another portion of the blood sample with a second staining reagent containing at least a second fluorescent dye. The first and second staining reagents can be same or different. The first and second fluorescent dyes can be same or different. They can be nucleic acid dyes. Examples of fluorescent dyes include but are not limited to propidium iodide, ethidium bromide, DAPI, Hoechst dyes, Acridine Orange, 7-AAD, LDS 751, TOTO families of dyes, TO-PRO families of dyes, SYTO family of dyes, Thiazole Orange, Basic Orange 21, Auramine-O, and the dye compounds disclosed in U.S. Pat. No. 6,004,816, etc., which is incorporated herein by reference in its entirety as if fully set forth.

In the detection unit, one measurement sample is first supplied to the flow cell to form a first sample flow; the first sample flow is illuminated with a first irradiation light; and the signals (e.g., fluorescence and scattered light with the forward angle) are measured with two detectors. After completing the measurement of the first sample flow, another measurement sample is then supplied to the flow cell to form a second sample flow; the second sample flow is illuminated with a second irradiation light; and the signals (e.g., fluorescence and scattered light with the forward angle) are measured with two detectors. The first and second irradiation lights can be same or different. The analysis unit analyzes the detected signals (e.g., fluorescence and scattered light) to obtain the information of the measurement samples, which includes but is not limited to one or more of the following parameters: the total count of the white blood cells, the counts and percentages of different subtypes of the white blood cells (e.g., lymphocytes, monocytes, neutrophils, eosinophils, and basophils, etc.), the total count of the red blood cells, the total count of the platelets, the sizes of individual red blood cells, the size distribution of the red blood cell population, the sizes of individual platelets, the size distribution of the platelet population, the count of reticulocyte cells, and the count of immature platelet cells, etc.

In some embodiments, a device or device system as described herein is used to analyze white blood cells, red blood cells and platelets in a blood sample. The sample supply unit prepares a first measurement sample by mixing a portion of the blood sample with a first reagent. The sample supply unit further prepares a second measurement sample by mixing a portion of the first measurement sample with a second reagent. The first reagent contains at least a fluorescent dye.

In the detection unit, the second measurement sample is first supplied to the flow cell to form a sample flow and two light signals (e.g., fluorescent light and scattered light with a forward angle) are measured by two detectors. The measured signals of the fluorescent light and scattered light are used by the signal analysis unit to determine the count of red blood cells, or the count of platelets, or both. After measuring the second measurement sample, the first measurement sample is then supplied to the flow cell to form a sample flow and two light signals (e.g., fluorescent light and scattered light with a forward angle) are measured by two detectors. The measured signals of the fluorescent light and scattered light are used by the signal analysis unit to determine the count of white blood cells, the count of different subtypes of white blood cells (e.g., lymphocytes, monocytes, neutrophils, eosinophils, and basophils, etc.), and the percentages of different subtypes of white blood cells (e.g., lymphocytes, monocytes, neutrophils, eosinophils, and basophils, etc.), etc. In other embodiments, the first measurement sample can be measured in the flow cell before the second measurement sample is measured in the flow cell.

When the collecting lens is used to collect both fluorescent light and scattered light, the efficiency of collecting light signals is an important consideration. For example, the fluorescent light usually has a low intensity and an optimized collection efficiency is important to improve the detection sensitivity and signal-to-noise ratio.

Figure 16A:
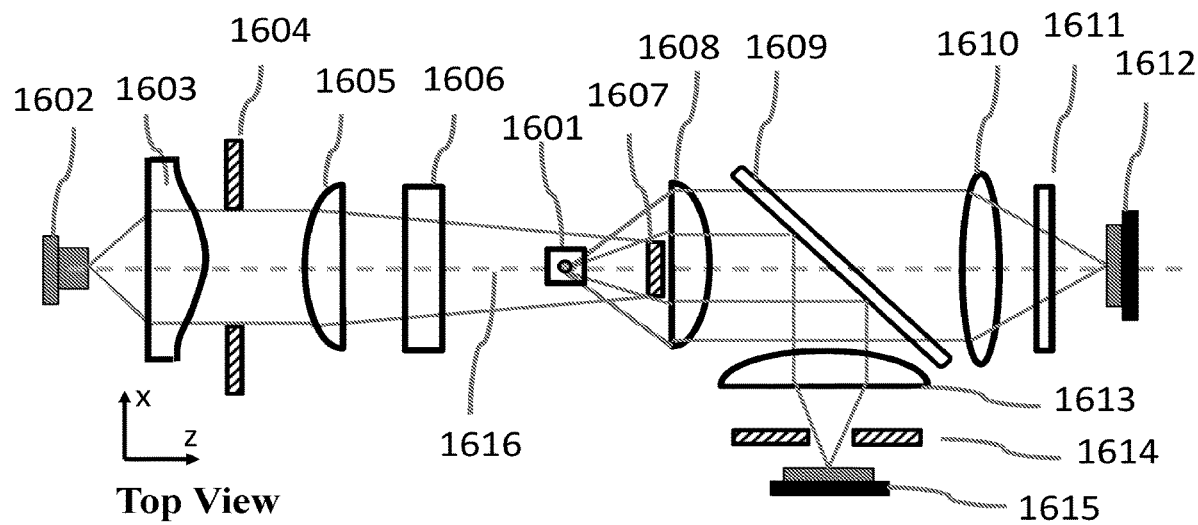
FIGS. 16A and 16B illustrate, in accordance with various embodiments of the disclosure, another non-limiting example of the detection unit.
Figure 16B:
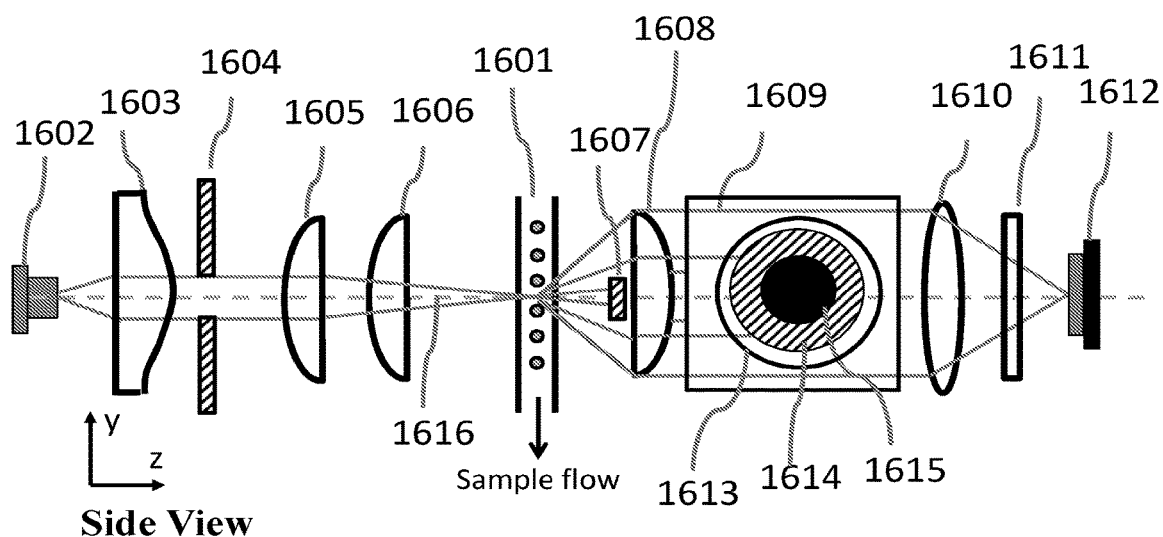

FIG. 16A (top view) and FIG. 16B (side view) show a non-limiting example of the detection unit. The measurement sample is formed into a sample flow in the flow cell 1601. A laser diode 1602 is used as the light source. The focusing module comprises an aspherical lens 1603, an aperture 1604, a spherical lens 1605 and a cylindrical lens 1606. The irradiation light emitted from the laser diode 1602 is first collimated by the aspherical lens 1603 into a parallel light, and further focused by the lens pair 1605 and 1606 into a light beam spot of elliptical shape on the flow cell. The aperture 1604 is used to define the diameter of the collimated light. A collection lens 1608 is used to collect the signal light from the flow cell into a collimated light. The detection module further comprises a beam stopper 1607 between the flow cell and the collecting lens to block the irradiation light. The receiving module comprises a beam splitter 1609, a focusing lens 1610, a filter 1611, a second focusing lens 1613, and an aperture 1614. The beam splitter 1609 separates the collimated signal light from the collecting lens into two optical paths. In one path, the signal light passes through the focusing lens 1610 and the filter 1611, and then is measured by a detector 1612. In the other path, the signal light passes through the focusing lens 1613 and the aperture 1614, and then is measured by a detector 1615. By choosing a long pass filter or band pass filter as the filter 1611, the detector 1612 measures the intensity of the fluorescent light from the sample flow. In some embodiments, the beam splitter 1609 is a dichroic mirror. In certain embodiments, the dichroic mirror has a pass band that matches with the wavelength of the fluorescent light.

The selection of the collecting lens 1608 and the focusing lens 1610 is important to increase the collection efficiency of the fluorescent light from the flow cell. First, the collecting lens 1608 limits the maximum amount of the fluorescent light that can be collected as the collimated light, and this maximum amount is determined by the numerical aperture of the collecting lens. Second, the selection of the collecting lens 1608 and the focusing lens 1610 determines the focused spot size of the fluorescent light reaching the detector 1612. The focused spot size depends on the spherical aberration introduced by the lens 1608 and the lens 1610. When this focused spot size is larger than the effective detecting area of the detector, the portion of the fluorescent light that is outside the effective detecting area is not measured by the detector. This decreases the detectable signal intensity and requires a more sensitive detector. Such an issue is particularly critical for detectors having a small effective detecting area (e.g., photodiode, avalanche photodiode (APD), and silicon photomultipliers (SiPM)). For example, an aspherical lens is used as the collecting lens in order to measure the fluorescent light with an avalanche photodiode (APD) as the detector (e.g., U.S. Pat. Nos. 7,894,047 and 7,580,120, which are incorporated herein by reference in their entirety as if fully set forth).

Figure 17:
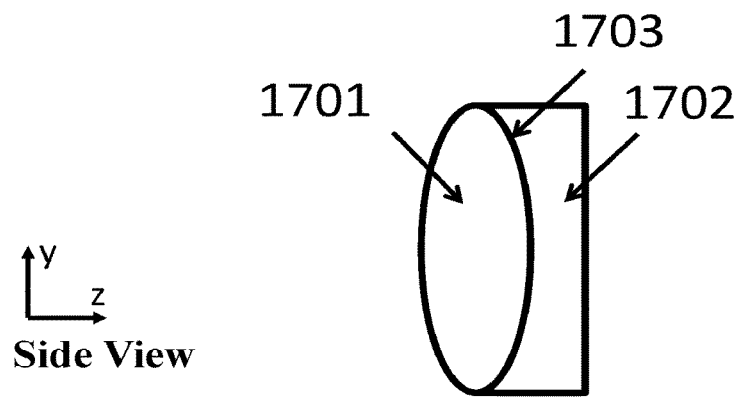
FIG. 17 illustrates an example embodiment of a doublet lens that may be used with any of the embodiments disclosed herein.

In one non-limiting example of a device or device system as described herein, a spherical lens is used as the collecting lens 1608 and a doublet lens is used as the focusing lens 1610 to achieve an optimal collection efficiency. A doublet lens is made of two simple lenses paired together. FIG. 17 shows a non-limiting example of a doublet lens, which comprises a first simple lens 1701 and a second simple lens 1702, which are paired together at the interface surface 1703. A doublet lens is normally used to reduce achromatic aberration, which means the aberration between different wavelengths of light. Here, a double lens is used to improve the collection efficiency of the fluorescent light in a device or device system as described herein.

Figure 18A:
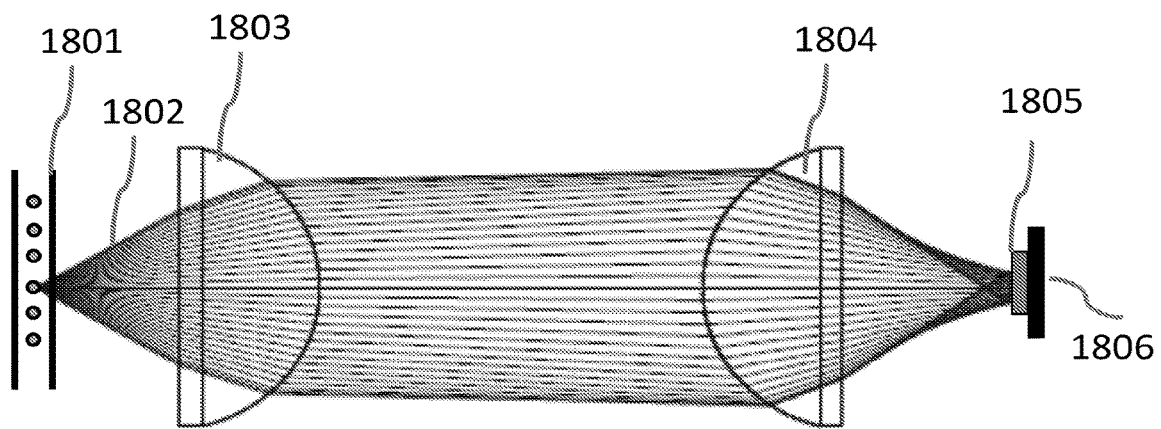
FIGS. 18A and 18B illustrate, in accordance with various embodiments of the disclosure, a non-limiting example of the detection unit, in which the collection efficiency is improved with a doublet lens.
Figure 18B:
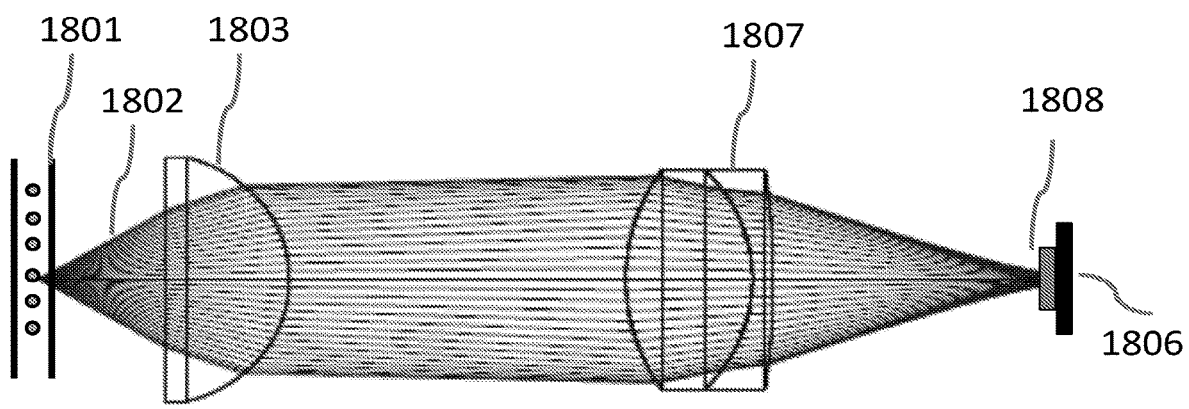

FIGS. 18A and 18B show a non-limiting example demonstrating the improvement of the collection efficiency with a doublet lens. In FIG. 18A, a spherical lens 1803 is used as the collecting lens to collect the fluorescent light signal 1802 from the flow cell 1801. Another spherical lens 1804 is used as the first focusing lens to focus the collected fluorescent light into a focused spot 1805 on the detector 1806. In comparison, as shown in FIG. 18B, a doublet lens 1807 is used as the first focusing lens, and the collected fluorescent light is focused into a focused spot 1808. The focused spot 1808 in FIG. 18B has a much smaller size as compared to the focused spot 1805 in FIG. 18A. Therefore, a detector with a smaller effective detection area can be used for the measurement with the doublet lens.

Figure 16C:
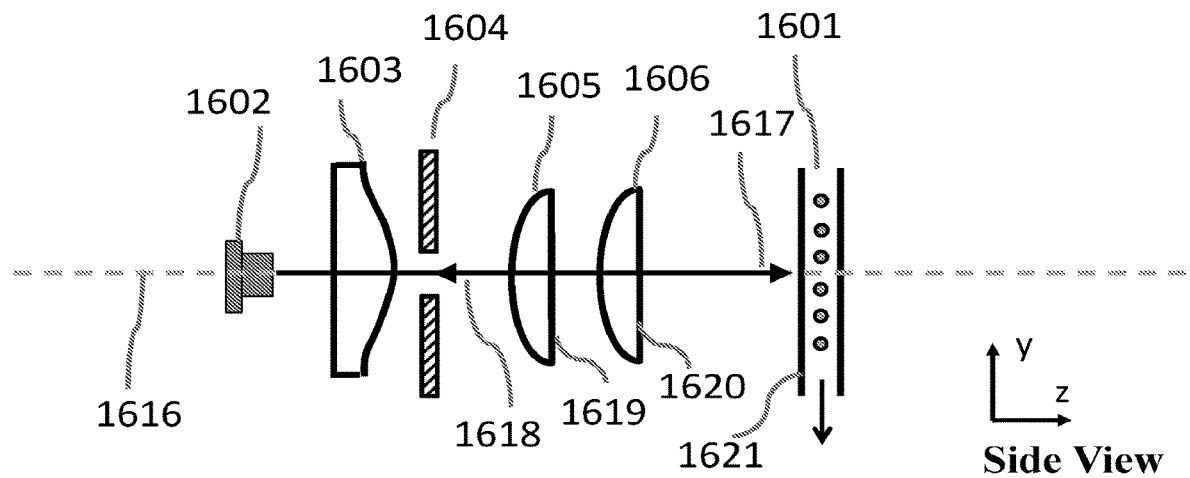
FIG. 16C illustrates, in accordance with various embodiments of the disclosure, a zoom-in view of the light source, the focusing module and the flow cell. In this non-limiting example, the optical axis of the spherical lens 1605 and the optical axis of the cylindrical lens 1606 are coaxial, and they are further coaxial with the center axis 1616 of the light emitted from the light source.

As shown in the non-limiting example of FIG. 16A and FIG. 16B, there are several surfaces in the irradiation light's path that may reflect a portion of the irradiation light back into the light source. FIG. 16C is the zoom-in view of the light source, the focusing module and the flow cell. In this configuration, a planar surface 1619 of the spherical lens 1605, a planar surface 1620 of the cylindrical lens 1606, and a planar surface 1621 of the flow cell 1601 may each reflect a portion of the irradiation light 1617 back towards the light source 1602. If this reflected light 1618 enters the light source, it may cause the intensity of the irradiation light to fluctuate. Some types of light source such as a laser diode are particularly susceptible to the interference from the reflected light. This fluctuation issue of light source, compounded with the fact that a replaceable or disposable made of low-cost plastic materials can reflect a significant amount of the irradiation light, can make a detection unit inaccurate for detection of particles and/or cells. Therefore, it is preferred that the reflection of the irradiation light is eliminated or minimized. For example, the reflected light can be directed away from the light source.

In some embodiments, the focusing module is configured to eliminate or minimize the reflection of the irradiation light from surfaces of components in the focusing module, a surface of the flow cell, or a surface in a cartridge device that hosts the flow cell. Non-limiting examples of a cartridge device that hosts a flow cell are described in U.S. patent application Ser. No. 15/803,133 and U.S. patent application Ser. No. 15/819,416, which are incorporated herein by reference in their entirety as if fully set forth. The cartridge device is received into a reader instrument for analysis. In some embodiments, the detection module is a component of the reader instrument. As a non-limiting example, to reduce the reflection of the irradiation light, an anti-reflection coating can be applied onto surfaces of components in the focusing module, a surface of the flow cell, or a surface in a cartridge device that hosts the flow cell.

In the configuration of FIG. 16C, the optical axis of the spherical lens 1605 and the optical axis of the cylindrical lens 1606 are coaxial. They are further coaxial with the center axis 1616 of the irradiation light emitted from the light source. In this configuration, the irradiation light 1617 is reflected by the surface 1621 of the flow cell 1601, and the reflected light 1618 is directed towards the light source 1602.

In some embodiments, the focusing module is configured to direct the reflection of the irradiation light away from the light source, or to block the reflection of the irradiation light from entering the light source.

Figure 16D:
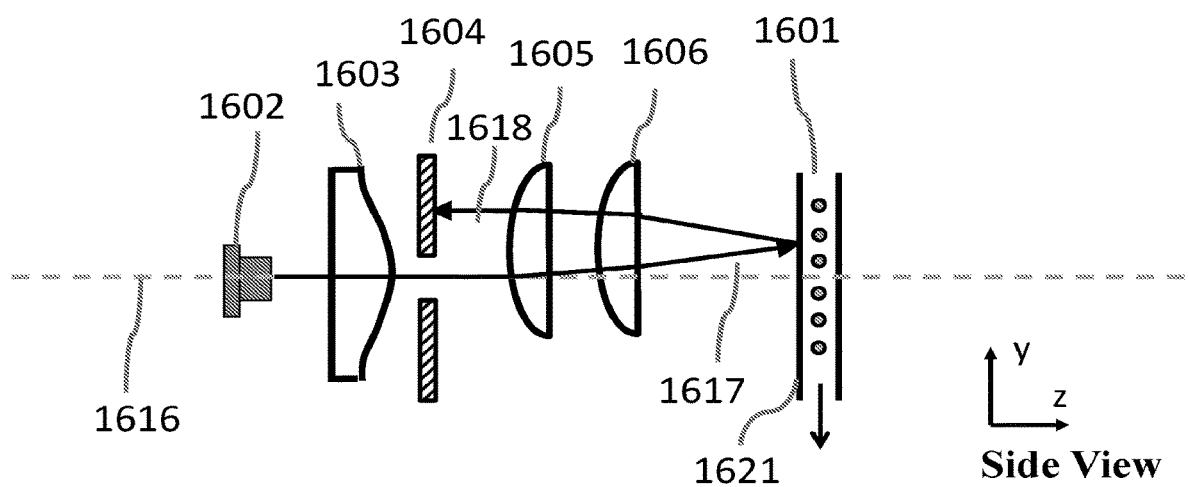
FIG. 16D illustrates, in accordance with various embodiments of the disclosure, a zoom-in view of the light source, the focusing module and the flow cell. In this non-limiting example, the optical axis of the spherical lens 1605 and the optical axis of the cylindrical lens 1606 are coaxial, but they are not coaxial with the center axis 1616 of the light emitted from the light source.
Figure 16E:
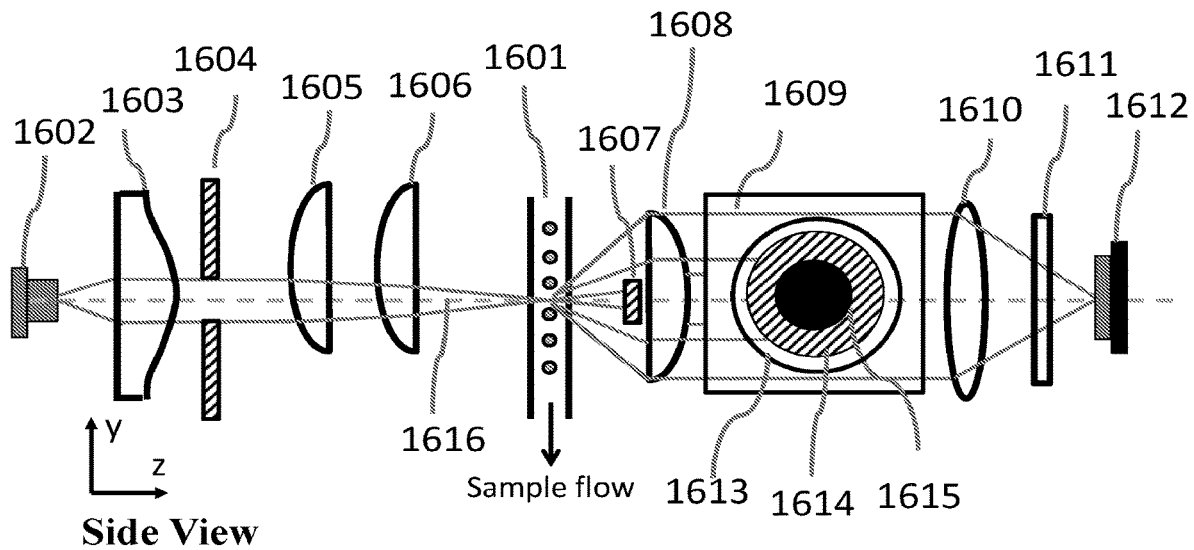
FIG. 16E illustrates, in accordance with various embodiments of the disclosure, a non-limiting example of a detection unit, in which the two lenses 1605 and 1606 are coaxial with each other, but not coaxial with the center axis 1616 of the light emitted from the light source 1602.

In a non-limiting example as shown FIG. 16D, the optical axis of the spherical lens 1605 and the optical axis of the cylindrical lens 1606 are coaxial. However, they are not coaxial with the center axis 1616 of the irradiation light emitted from the light source. In this way, the reflected light 1618 is directed away from the light source and blocked by the aperture 1604 from entering the light source. FIG. 16E shows the overview of the detection unit with the two lenses 1605 and 1606 being coaxial with each other, but not coaxial with center axis 1616 of the irradiation light emitted from the light source 1602.

Figure 16F:
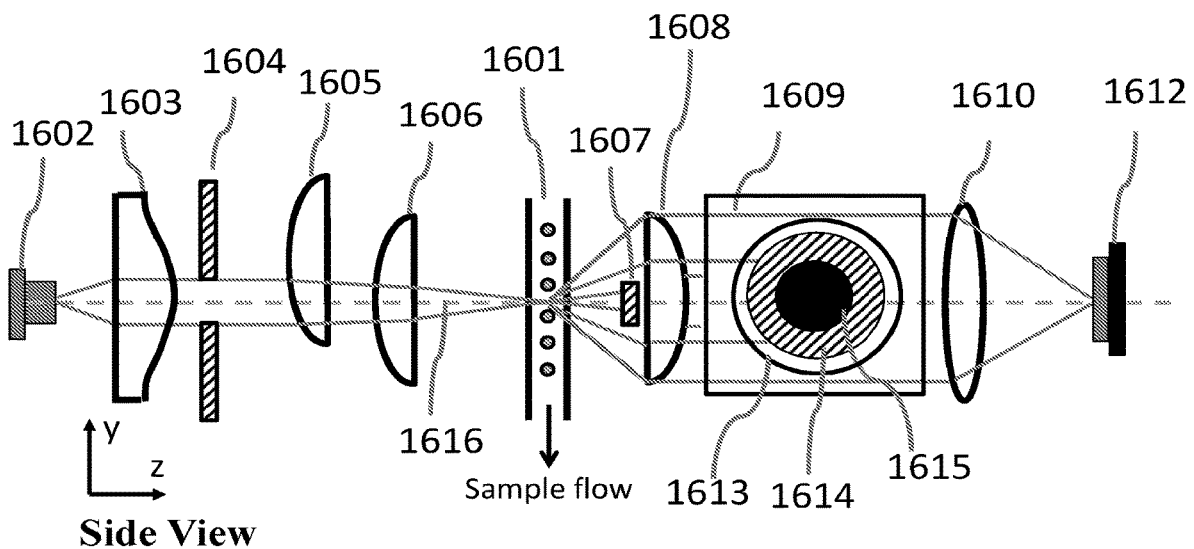
FIG. 16F illustrates, in accordance with various embodiments of the disclosure, a non-limiting example of a detection unit, in which the lens 1606 is coaxial with the center axis 1616 of the emitted light, but the lens 1605 is not coaxial with the center axis 1616 of the emitted light.

FIG. 16F shows another non-limiting example, in which the lens 1606 is coaxial with the center axis 1616 of the irradiation light, but the lens 1605 is not coaxial with the center axis 1616 of the irradiation light. In this configuration, the reflection of the irradiation light by a surface of the flow cell or a surface in a cartridge device that hosts the flow cell can be directed away and blocked by the aperture 1604 from entering the light source 1602.

Other configurations can also work, if they include at least one lens not coaxial with the irradiation light's center axis. For example, if the lens 1606 is not coaxial with the center axis 1616 of the irradiation light, but the lens 1605 is coaxial with the center axis 1616 of the irradiation light, the reflection of the irradiation light by a surface of the flow cell or a surface in a cartridge device that hosts the flow cell can also be directed away and blocked by the aperture 1604 from entering the light source 1602.

In various embodiments, one or more optical components in the focusing module are positioned not coaxial with the center axis of the irradiation light emitted from the light source. In some embodiments, such an optical component being not coaxial comprises a cylindrical lens, a spherical lens, or both. In some embodiments, the optical axis of such an optical component being not coaxial is positioned away from the center axis of the irradiation light in the range of about 0.01 to 0.1, 0.1 to 1, 1-2, 2-3, 3-4, 4-5, 5-6, 6-7, 7-8, 8-9, 9-10, 10-20, 20-30, 30-40, 40-50, 50-60, 60-70, 70-80, 80-90, or 90-100 mm. In various embodiments, an aperture is used in the focusing module to block reflected irradiation light from entering the light source. The size of transparent area of the aperture needs to be large enough to define the diameter of the collimated irradiation light, and small enough to block the reflected irradiation light. In some embodiments, the diameter of the transparent area of the aperture is in the range of about 0.1 to 1, 1-2, 2-3, 3-4, 4-5, 5-6, 6-7, 7-8, 8-9, 9-10, 10-20, 20-30, 30-40, 40-50, 50-60, 60-70, 70-80, 80-90, or 90-100 mm.

Figure 16G:
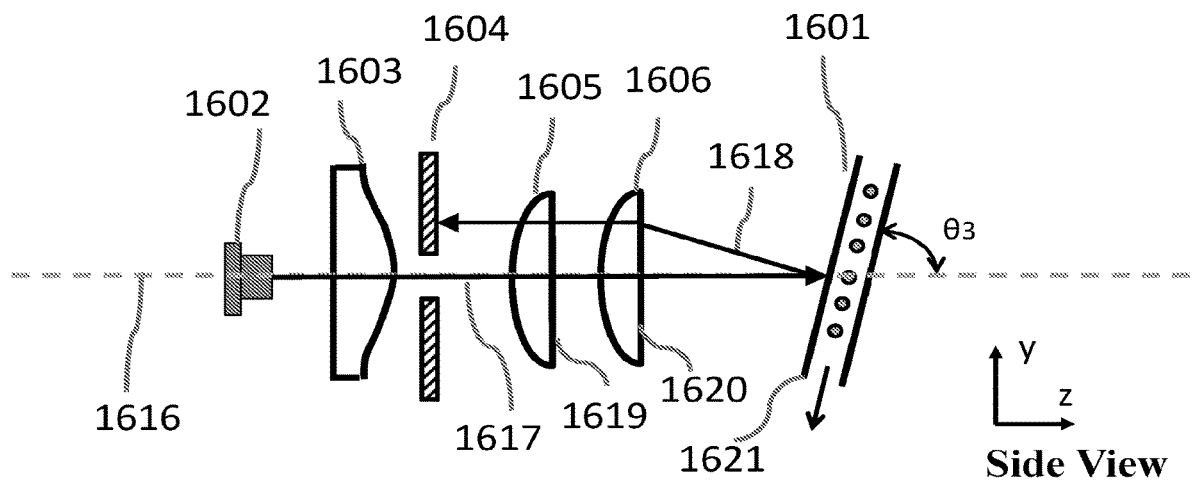
FIG. 16G illustrates, in accordance with various embodiments of the disclosure, a zoom-in view of the light source, the focusing module and the flow cell. In this non-limiting example, the flow cell 1601 is tilted in a way that the surface 1621 of the flow cell is not perpendicular to the irradiation light 1617. For example, the angle $\theta_3$ between the surface 1621 and the center axis 1616 of the irradiation light 1617 is not equal to 90 degrees.

In some embodiments, other configurations of the focusing module can also be used to direct the reflected irradiation light away from the light source. A non-limiting example is shown in FIG. 16G, in which the flow cell 1601 is tilted in a way that the surface 1621 of the flow cell is not perpendicular to the irradiation light 1617. For example, the angle $\theta_3$ between the surface 1621 and the center axis 1616 of the irradiation light 1617 is not equal to 90 degrees, and can be about 45-50, 50-55, 55-60, 60-65, 65-70, 70-75, 75-80, 80-85, 85-89, or 89-89.9 degrees. In this way, the reflected light 1618 is directed away and blocked by the aperture 1604 from entering the light source 1602. In various embodiments, the flow cell or the cartridge device that hosts the flow cell is positioned or titled in such an orientation that a reflective surface of the flow cell or the cartridge device is not perpendicular to the central axis of the irradiation light and directs the reflected light away from the light source. In some other embodiments, a lens in the focusing module is positioned or titled in such an orientation that the surface of the lens is not perpendicular to the central axis of the irradiation light and directs the reflected light away from the light source.

Various embodiments of the present disclosure provide a device or device system. The device or device system comprises: a flow cell configured to form a sample flow of a measurement sample; a light source configured to emit an irradiation light for illuminating the sample flow; a collecting lens configured to collect both a scattered light with a forward angle and a fluorescent light from the sample flow; a first light detector configured to detect the collected scattered light; and a second light detector configured to detect the collected fluorescent light.

Various embodiments of the present disclosure provide a device or device system for analyzing cells (e.g., blood cells). The device or device system comprises: a flow cell configured to form a sample flow of a measurement sample comprising cells; a light source configured to emit an irradiation light for illuminating the sample flow; a collecting lens configured to collect both a scattered light with a forward angle and a fluorescent light from the sample flow; a first light detector configured to detect the collected scattered light; and a second light detector configured to detect the collected fluorescent light. In various embodiments, the cells are blood cells. In some embodiments, the cells are white blood cells, red blood cells, or platelet cells, or combinations thereof. In some embodiments, the cells are lymphocytes, monocytes, neutrophils, eosinophils, or basophils, or combinations thereof. In various embodiments, the blood cells are labeled with a fluorescent dye. In various embodiments, the fluorescent dye is a nucleic acid dye.

In various embodiments, the irradiation light forms an elliptical beam spot on the sample flow. In various embodiments, the major axis ($d_2$) of the elliptical beam spot is perpendicular to the direction of the sample flow and the minor axis ($d_1$) of the elliptical beam spot is along the direction of the sample flow. In some embodiments, the $d_2$:$d_1$ ratio is more than 1. In some embodiments, the $d_2$:$d_1$ ratio is about 2-5. In some embodiments, the $d_2$:$d_1$ ratio is about 5-10. In some embodiments, the $d_2:d_1$ ratio is about 10-15. In some embodiments, the $d_2:d_1$ ratio is about 15-20. In some embodiments, the $d_2:d_1$ ratio is about 20-25. In some embodiments, the $d_2:d_1$ ratio is about 25-40. In various embodiments, $d_2$ is about 5-10, 10-15, 15-20, 20-25, 25-40, or 40-60 times of the sample flow's width ($d_3$). In various embodiments, a device or device system as described herein further comprises a focusing module configured to shape the irradiation light into an elliptical beam spot on the sample flow. In some embodiments, the focusing module comprises one cylindrical lens. In other embodiments, the focusing module comprises two cylindrical lenses, wherein the two cylindrical lenses are so positioned that their cylinder axes are perpendicular to each other. In still other embodiments, the focusing module comprises more than two cylindrical lenses. In various embodiments, the focusing module comprises a cylindrical lens, an anamorphic prism pair, or a diffraction grating component, or combinations thereof.

In various embodiments, the collecting lens of the detection unit is used to collect both a fluorescent light and a scattered light. In some embodiments, the collecting lens of the detection unit is used to collect both a fluorescent light and a forward scattered light (i.e., a scattered light with a forward angle (e.g., a scattering angle less than about 25 degrees)). In embodiments, the collecting lens of the detection unit is used to collect both a fluorescent light and a side scattered light (i.e., a scattered light with a side angle (e.g., a scattering angle more than about 25 degrees)).

In various embodiments, the scattered light collected by the collecting lens comprises a scattered light with a forward angle. In various embodiments, the scattered light collected by the collecting lens comprises a scattered light with a scattering angle less than about 3, 4, 5, 6, 7, 8, 9, 10, 11, 12, 13, 14, 15, 16, 17, 18, 19, 20, 21, 22, 23, 24, or 25 degrees. In various embodiments, the scattered light detected by the first detector comprises a scattered light with a forward angle. In various embodiments, the scattered light detected by the first detector comprises a scattered light with a scattering angle less than about 3, 4, 5, 6, 7, 8, 9, 10, 11, 12, 13, 14, 15, 16, 17, 18, 19, 20, 21, 22, 23, 24, or 25 degrees. In some embodiments, the collected scattered light comprises light from elastic scattering. In some embodiments, the collected scattered light comprises light from non-elastic scattering.

In various embodiments, the scattered light collected by the collecting lens comprises a scattered light with a side angle. In various embodiments, the scattered light collected by the collecting lens comprises a scattered light with a scattering angle more than about 25, 30, 35, 40, 45, 50, 55, 60, 65, 70, 75, 80, 85, or 90 degrees. In various embodiments, the scattered light detected by the first detector comprises a scattered light with a side angle. In various embodiments, the scattered light detected by the first detector comprises a scattered light with a scattering angle more than about 25, 30, 35, 40, 45, 50, 55, 60, 65, 70, 75, 80, 85, or 90 degrees. In some embodiments, the collected scattered light comprises light from elastic scattering. In some embodiments, the collected scattered light comprises light from non-elastic scattering.

In various embodiments, the detection unit can measure both a fluorescent light and a side scattered light to analyze particles and/or cells in a sample flow. A non-limiting example of such an analysis method is disclosed in U.S. Pat. No. 7,894,047, which is incorporated herein by reference in its entirety as if fully set forth. In such an example, an analyzer uses a collecting lens to collect both a fluorescent light and a side scattered light, and further measures them to analyze white blood cells in a sample.

In various embodiments, the detection unit can measure both a fluorescent light and a forward scattered light to analyze particles and/or cells in a sample flow. A non-limiting example of such an analysis method is disclosed in U.S. Pat. No. 6,004,816, which is incorporated herein by reference in its entirety as if fully set forth.

In certain embodiments, the collecting lens is one lens. In some embodiments, one collecting lens is configured to collect both a scattered light with a forward angle and a fluorescent light from the sample flow. In various embodiments, the collected scattered light and the collected fluorescent light are detected with two separated detectors. In various embodiments, the collected scattered light and the collected fluorescent light are split into two separate optical paths.

In various embodiments, the second light detector comprises a bipolar phototransistor, a photosensitive field-effect transistor, a photomultiplier tube, an avalanche photodiode, a photodiode, a CCD device, or a CMOS device, or combinations thereof.

In various embodiments, a device or device system as described herein further comprises a receiving module configured to split the collected scatter light and the collected fluorescent light into two separate optical paths. In various embodiments, the receiving module comprises a dichroic mirror for splitting the collected scatter light and the collected fluorescent light into two separate optical paths. In some embodiments, the receiving module reflects the scattered light to the first light detector and transmits the fluorescent light to the second light detector. In other embodiments, the receiving module transmits the scattered light to the first light detector and reflects the fluorescent light to the second light detector.

In some embodiments, the sample flow irradiated by the beam spot is formed in a flow cell without sheath flow (i.e., a sheathless flow cell). Examples of the sheathless flow cell include but are not limited to those disclosed in U.S. Patent Application No. 62/497,075, U.S. patent application Ser. No. 15/803,133, and U.S. patent application Ser. No. 15/819,416, which are incorporated herein by reference in their entirety as if fully set forth. In other embodiments, the sample flow irradiated by the beam spot is formed in a flow cell with sheath flow.

In some embodiments, the irradiation light is a Gaussian beam. In various embodiments, the light source comprises a laser diode, a LED device, or a halogen lamp, or combinations thereof. In various embodiments, the light source comprises: a light-emitting component configured to emit a light; an optical fiber; and a condenser lens configured to focus the light into one end of the optical fiber, whereby the light exits the other end of the optical fiber. In various embodiments, the light-emitting component comprises a laser diode, a LED device, or a halogen lamp, or combinations thereof. In some embodiments, the optical fiber is a single-mode optical fiber.

In various embodiments, a device or device system as described herein further comprises a beam stopper between the sample flow and the collecting lens, wherein the beam stopper is configured to block the irradiation light. In various embodiments, a device or device system as described herein further comprises a beam stopper behind the collecting lens, wherein the beam stopper is configured to block the irradiation light.

In various embodiments, a device or device system as described herein further comprises an aperture on the scattered optical path from the sample flow to the first light detector, wherein the aperture is configured to limit the scattered light entering the first light detector.

Various embodiments of the present disclosure provide a method. This method comprises: forming a sample flow of a measurement sample using a flow cell; illuminating the sample flow using an irradiation light emitted from a light source; collecting both a scattered light with a forward angle and a fluorescent light from the sample flow using a collecting lens; detecting the collected scattered light using a first light detector; and detecting the collected fluorescent light using a second light detector. In some embodiments, this method is performed twice or more times using the same flow cell. In certain embodiments, the collecting lens is one lens. Various embodiments of the present disclosure provide a method. This method, comprises: forming a first sample flow of a first measurement sample using a flow cell; illuminating the first sample flow using an irradiation light emitted from a light source; collecting both a scattered light with a forward angle and a fluorescent light from the first sample flow using a collecting lens; detecting the collected scattered light using a first light detector; detecting the collected fluorescent light using a second light detector; forming a second sample flow of a second measurement sample using the same flow cell; illuminating the second sample flow using the irradiation light emitted from the light source; collecting both a scattered light with a forward angle and a fluorescent light from the second sample flow using the collecting lens; detecting the collected scattered light using a first light detector; and detecting the collected fluorescent light using a second light detector. In certain embodiments, the collecting lens is one lens.

Various embodiments of the present disclosure provide a method for analyzing cells (e.g., blood cells). This method comprises: forming a sample flow of a measurement sample comprising cells using a flow cell; illuminating the sample flow using an irradiation light emitted from a light source; collecting both a scattered light with a forward angle and a fluorescent light from the sample flow using a collecting lens; detecting the collected scattered light using a first light detector; and detecting the collected fluorescent light using a second light detector. In certain embodiments, the collecting lens is one lens. In various embodiments, the cells are blood cells. In some embodiments, the cells are white blood cells, red blood cells, or platelet cells, or combinations thereof. In some embodiments, the cells are lymphocytes, monocytes, neutrophils, eosinophils, or basophils, or combinations thereof. In various embodiments, the blood cells are labeled with a fluorescent dye. In certain embodiments, the fluorescent dye is a nucleic acid dye. In some embodiments, this method is preformed twice or times using the same flow cell.

Various embodiments of the present disclosure provide a method for analyzing cells (e.g., blood cells). This method, comprises: forming a first sample flow of a first measurement sample comprising cells using a flow cell; illuminating the first sample flow using an irradiation light emitted from a light source; collecting both a scattered light with a forward angle and a fluorescent light from the first sample flow using a collecting lens; detecting the collected scattered light using a first light detector; detecting the collected fluorescent light using a second light detector; forming a second sample flow of a second measurement sample comprising cells using the same flow cell; illuminating the second sample flow using the irradiation light emitted from the light source; collecting both a scattered light with a forward angle and a fluorescent light from the second sample flow using the collecting lens; detecting the collected scattered light using a first light detector; and detecting the collected fluorescent light using a second light detector. In certain embodiments, the collecting lens is one lens.

In various embodiments, the cells in the first measurement sample are labeled with a fluorescent dye. In certain embodiments, the fluorescent dye is a nucleic acid dye. In various embodiments, the cells in the first measurement sample are blood cells. In some embodiments, the cells in the first measurement sample are white blood cells, red blood cells, or platelet cells, or combinations thereof. In some embodiments, the cells in the first measurement sample are lymphocytes, monocytes, neutrophils, eosinophils, or basophils, or combinations thereof. In various embodiments, the blood cells in the first measurement sample are labeled with a fluorescent dye. In various embodiments, the cells in the second measurement sample are labeled with a fluorescent dye. In certain embodiments, the fluorescent dye is a nucleic acid dye. In various embodiments, the cells in the second measurement sample are blood cells. In some embodiments, the cells in the second measurement sample are white blood cells, red blood cells, or platelet cells, or combinations thereof. In some embodiments, the cells in the second measurement sample are lymphocytes, monocytes, neutrophils, eosinophils, or basophils, or combinations thereof.

In some embodiments, a method as described herein further comprises preparing a measurement sample by mixing a sample with a first staining and/or dilution reagent.

In various embodiments, a method as described herein further comprises using the detected signals of the scattered light and/or the fluorescent light to analyze the cells (e.g., blood cells) in the measurement sample.

In various embodiments, a method as described herein further comprises splitting the collected scattered light and the collected fluorescent light into two separate optical paths.

In various embodiments, a method as described herein further comprises blocking the irradiation light using a beam stopper between the sample flow and the collecting lens. In various embodiments, a method as described herein further comprises blocking the irradiation light using a beam stopper behind the collecting lens.

In various embodiments, the measurement sample comprises cells, or particles, or combinations thereof. Examples of the cells include but are not limited to blood cells. Examples of the particles include but are not limited to liquid droplets, molecules (e.g., nucleic acid molecules, protein molecules, etc.), viruses, and beads. In some embodiments, the measurement sample comprises white blood cells, red blood cells, or platelet cells, or combinations thereof. In some embodiments, the measurement sample comprises lymphocytes, monocytes, neutrophils, eosinophils, or basophils, or combinations thereof. In some embodiments, the measurement sample comprises liquid droplets, molecules (e.g., nucleic acid molecules, protein molecules, etc.), viruses, or beads, or combinations thereof. In various embodiments, the cells are labeled with a fluorescent dye. In various embodiments, the particles are either fluorescent or labeled with a fluorescent dye. In various embodiments, a method as described herein further comprises labeling the cells with a fluorescent dye.

Various embodiments of the present disclosure provide a device or device system comprising: a flow cell for forming a sample flow from a measurement sample; a light source for emitting an irritation light to irradiate the measurement sample in the flow cell; a focusing module for focusing the irradiation light into a beam spot of elliptical shape on the flow cell; a collecting lens for collecting both the fluorescence and the scattered light from the measurement sample; a receiving module for splitting the collected light into at least two optical paths, wherein the light in one optical path comprises the scattered light and is detected by a first detector, and the light in another optical path comprise the fluorescence and is detected by a second detector; and an analysis unit that analyzes the signals from the first and/or second detectors to obtain information of the measurement sample. In various embodiments, the analyzed signals include at least one of the two signals: the signal detected by the first detector and the signal detected by the second detector. In various embodiments, the measurement sample is a blood sample.

The range of the scattered light detected by the first detector can be selected, for example, by adjusting the configuration of the collecting lens (e.g., its size, its distance from the sample flow, and its orientation in relation to the direction of the irradiation light). In various embodiments, the collecting lens is positioned substantially facing the direction of the irradiation light. In various embodiments, the scattered light detected by the first detector comprises a scattered light with a forward angle (i.e., a forward-angle scattered light). In various embodiments, the scattered light detected by the first detector comprises a scattered light with a scattering angle less than about 3 degrees. In various embodiments, the scattered light detected by the first detector comprises a scattered light with a scattering angle less than about 5 degrees. In various embodiments, the scattered light detected by the first detector light comprises a scattered light with a scattering angle less than about 10 degrees. In various embodiments, the scattered light detected by the first detector comprises a scattered light with a scattering angle less than about 15 degrees. In various embodiments, the scattered light detected by the first detector comprises a scattered light with a scattering angle less than about 20 degrees.

In various embodiments, the elliptical beam spot on the flow cell has a diameter of about 4-5, 5-10, 10-20, 20-30, 30-40, 40-50, 50-60, 60-70, 70-80, 80-90, 90-99, or 99-100 μm in the direction parallel to the sample flow, and a diameter of about 40-100, 100-500, 500-1000, 1000-1500, 1500-2000, 2000-2500, 2500-3000, 3000-3500, 3500-4000, 4000-4500, or 4500-5000 μm in the direction perpendicular to the sample flow. In various embodiments, the sample flow formed in the flow cell has a width of about 4-5, 5-10, 10-20, 20-30, 30-40, 40-50, 50-60, 60-70, 70-80, 80-90, or 90-100 μm in the direction perpendicular to the sample flow.

In some embodiments, the sample flow irradiated by the beam spot is formed in a flow cell without sheath flow (i.e., a sheathless flow cell). Examples of the sheathless flow cell include but are not limited to those disclosed in U.S. Patent Application No. 62/497,075, U.S. patent application Ser. No. 15/803,133, and U.S. patent application Ser. No. 15/819,416, which are incorporated herein by reference in their entirety as if fully set forth. In other embodiments, the sample flow irradiated by the beam spot is formed in a flow cell with sheath flow.

In various embodiments, the focusing module comprises at least one cylindrical lens. In various embodiments, the focusing module comprises an anamorphic prism pair.

In various embodiments, the collecting lens is an aspherical lens. In various embodiments, the device or device system further comprises a beam stopper for blocking the irradiation light. In various embodiments, the beam stopper is positioned in the optical path from the collecting lens to one of the two detectors. In various embodiments, the beam stopper is positioned in the optical path from the flow cell to the collecting lens. In various embodiments, the beam stopper is an obstruction bar comprising light blocking material. In various embodiments, the obstruction bar has a bar width that blocks the irradiation light and the scattered light with a scattering angle less than about 1, 3, or 5 degrees.

In various embodiments, the light source comprises a laser diode, a LED device, or a halogen lamp. In various embodiments, the light source comprises a light-emitting component configured to emit a light, an optical fiber, and a condenser configured to focus the light into one end of the optical fiber, whereby the light exiting from the other end of the optical fiber is capable of irradiating the measurement sample. In various embodiments, the light-emitting component is a laser diode, a LED device, or a halogen lamp. In various embodiments, the detector for detecting the fluorescence comprises a photodiode. In various embodiments, the irradiation light is a Gaussian beam.

In various embodiments, a device or device system as described herein further comprises a sample supply unit configured to prepare a measurement sample by mixing a sample with a staining and/or dilution reagent. In various embodiments, the dilution reagent comprises at least one osmolarity-adjusting compound. In various embodiments, the staining reagent comprises at least one fluorescent dye. In various embodiments, the fluorescent dye is a nucleic acid dye, which selectively bind to nucleic acids. In various embodiments, the staining reagent further comprises a lysing compound that lyses red blood cells. In various embodiments, the staining reagent further comprises a sphering compound that spherizes red blood cells. In various embodiments, the dilution reagent further comprises a sphering compound that spherizes red blood cells. In various embodiments, the sample is a blood sample.

In various embodiments, a device or device system as described herein can be used to analyze blood samples and obtain information on blood cells in the blood sample. In various embodiments, the analysis unit classifies the white blood cells in the measurement sample into one or more subtypes including but not limited to lymphocytes, monocytes, neutrophils, eosinophils, and basophils. In various embodiments, the analysis unit classifies the blood cells in the measurement sample into red blood cells and platelets.

Various embodiments for the present disclosure provide a method for analyzing a blood sample. The method comprises: preparing at least one measurement sample by mixing a portion or the whole of the blood sample with a staining and/or dilution reagent; forming a sample flow of the measurement sample in a flow cell; focusing an irradiation light from a light source into an elliptical beam spot on the sample flow in the flow cell; collecting both the fluorescence and the scattered light from the measurement sample using one collecting lens; splitting the collected light from the collecting lens into at least two optical paths, wherein the light in one optical path comprise the scattered light and is detected by a first detector, and the light in another optical path comprises the fluorescence and is detected by a second detector; and analyzing the signals from the detectors to obtain information of the blood cells in the measurement sample. In various embodiments, the analyzed signals include at least one of the two signals: the signal detected by the first detector and the signal detected by the second detector. In various embodiments, the scattered light detected by the first detector comprises a scattered light with a forward angle (i.e., a forward-angle scattered light). In various embodiments, the scattered light detected by the first detector comprises a scattered light with a scattering angle less than about 3 degrees. In various embodiments, the scattered light detected by the first detector comprises a scattered light with a scattering angle less than about 5 degrees. In various embodiments, the scattered light detected by the first detector light comprises a scattered light with a scattering angle less than about 10 degrees. In various embodiments, the scattered light detected by the first detector comprises a scattered light with a scattering angle less than about 15 degrees. In various embodiments, the scattered light detected by the first detector comprises a scattered light with a scattering angle less than about 20 degrees.

In various embodiments, the method further comprises classifying the blood cells into one or more cell types including but not limited to white blood cells, red blood cells, and platelets. In some embodiments, the method further comprises classifying the blood cells into red blood cells and platelets. In various embodiments, the method further comprises classifying the white blood cells in one measurement sample into one or more subtypes including but not limited to lymphocytes, monocyte, neutrophils, eosinophils, and basophils. In various embodiments, the red blood cells are lysed, for example, in the measurement sample prepared for analyzing the white blood cells. In various embodiments, the method further comprises preparing at least one measurement sample by mixing a portion or the whole of the blood sample with a lysing compound, whereby the red blood cells are lysed in the measurement sample. In various embodiments, the method further comprises preparing at least one measurement sample by mixing a portion or the whole of the blood sample with a sphering compound, whereby the red blood cells are spherized in the measurement sample.

In various embodiments, a method described herein comprises: preparing a first measurement sample by mixing blood with a first staining and/or dilution reagent; forming a first sample flow of the first measurement sample in the flow cell; analyzing the signals from the detectors to obtain information of the while blood cells in the first measurement sample; preparing a second measurement sample by mixing blood with a second staining and/or dilution reagent; forming a second sample flow of the second measurement sample in the flow cell; and analyzing the signals from the detectors to obtain information of the red blood cells and platelets in the first measurement sample, wherein the first and second samples flows are formed separately in the flow cell. In various embodiments, the obtained information of the white blood cells includes at least one of the following parameters: the number of total white blood cells, the number of lymphocyte cells, the number of monocyte cells, the number of neutrophil cells, the number of eosinophil cells, and the number of basophil cells. In various embodiments, the obtained information of the red blood cells and platelets includes at least one of the following parameters: the number of red blood cells, the number of platelets, the sizes of individual red blood cells, the size distribution of the red blood cell population, the sizes of individual platelets, the size distribution of the platelet population, the number of reticulocyte cells, and the number of immature platelet cells, etc.

In accordance with the present disclosure, the terms "first" and "second" are used to designate identities but not to indicate any chronological sequence.

Many variations and alternative elements have been disclosed in embodiments of the present disclosure. Still further variations and alternate elements will be apparent to one of skill in the art. Among these variations, without limitation, are the selection of fluidic units, components and structures for the inventive devices and methods, and the samples that may be analyzed therewith. Various embodiments of the disclosure can specifically include or exclude any of these variations or elements.

In some embodiments, the numbers expressing quantities of ingredients, properties such as concentration, reaction conditions, and so forth, used to describe and claim certain embodiments of the disclosure are to be understood as being modified in some instances by the term "about." As one non-limiting example, one of ordinary skill in the art would generally consider a value difference (increase or decrease) no more than 10% to be in the meaning of the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the disclosure are approximations, the numerical values set forth in the specific examples are reported as precisely as practicable. The numerical values presented in some embodiments of the disclosure may contain certain errors necessarily resulting from the standard deviation found in their respective testing measurements.

Groupings of alternative elements or embodiments of the disclosure disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The disclosure is explained by various examples, which are intended to be purely exemplary of the disclosure, and should not be considered as limiting the disclosure in any way. Various examples are provided to better illustrate the claimed disclosure and are not to be interpreted as limiting the scope of the disclosure. To the extent that specific materials are mentioned, it is merely for purposes of illustration and is not intended to limit the disclosure. One skilled in the art may develop equivalent means or reactants without the exercise of inventive capacity and without departing from the scope of the disclosure.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the disclosure are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the disclosure known to the applicant at this time of filing the application has been presented and is intended for the purposes of illustration and description. The present description is not intended to be exhaustive nor limit the disclosure to the precise form disclosed and many modifications and variations are possible in the light of the above teachings. The embodiments described serve to explain the principles of the disclosure and its practical application and to enable others skilled in the art to utilize the disclosure in various embodiments and with various modifications as are suited to the particular use contemplated. Therefore, it is intended that the disclosure not be limited to the particular embodiments disclosed for carrying out the disclosure.

While particular embodiments of the present disclosure have been shown and described, it will be obvious to those skilled in the art that, based upon the teachings herein, changes and modifications may be made without departing from this disclosure and its broader aspects and, therefore, the appended claims are to encompass within their scope all such changes and modifications as are within the true spirit and scope of this disclosure.

Additional Aspects of the Present Disclosure

Aspects of the subject matter described herein may be useful alone or in combination with any one or more of the other aspect described herein. Without limiting the foregoing description, in a first aspect of the present disclosure, a device or device system comprises: a flow cell configured to form a sample flow of a measurement sample, wherein the measurement sample comprises particles and/or cells; a light source configured to emit an irradiation light for illuminating the sample flow; a collecting lens configured to collect both a scattered light with a forward angle and a fluorescent light from the particles and/or cells in the sample flow; and one, two, or more detectors configured to detect a signal of the scattered light with a forward angle and a signal of the fluorescent light.

In accordance with a second aspect of the present disclosure, which may be used in combination with any other aspect or combination of aspects listed herein, a device or device system as described herein further comprises a focusing module configured to focus the irradiation light to form an elliptical beam spot on the sample flow.

In accordance with a third aspect of the present disclosure, which may be used in combination with any other aspect or combination of aspects listed herein, a device or device system as described herein further comprises a focusing module that comprises a lens that is either not coaxial or not perpendicular with the central axis of irradiation light.

In accordance with a fourth aspect of the present disclosure, which may be used in combination with any other aspect or combination of aspects listed herein, the collected and/or detected scattered light includes a scattered light with a scattering angle less than about 3, 4, 5, 6, 7, 8, 9, 10, 11, 12, 13, 14, 15, 16, 17, 18, 19, 20, 21, 22, 23, 24, or 25 degrees.

In accordance with a fifth aspect of the present disclosure, which may be used in combination with any other aspect or combination of aspects listed herein, the flow cell is part of a cartridge device configured to be placed into a reader instrument for analysis, and wherein the reader instrument comprises a light source, a collecting lens, detectors, and a signal analysis unit.

In accordance with a sixth aspect of the present disclosure, which may be used in combination with any other aspect or combination of aspects listed herein, the cartridge device is configured to mix a sample with a reagent to form the measurement sample and to form a sample flow of the measurement sample in the flow cell.

In accordance with a seventh aspect of the present disclosure, which may be used in combination with any other aspect or combination of aspects listed herein, a device or device system as described herein further comprises a receiving module configured to split the scattered light with a forward angle and the fluorescent light collected by the collecting lens into two separate optical paths toward two separate detectors, respectively.

In accordance with an eighth aspect of the present disclosure, which may be used in combination with any other aspect or combination of aspects listed herein, a device or device system as described herein further comprises a doublet lens configured to focus the collected fluorescent light.

In accordance with a ninth aspect of the present disclosure, which may be used in combination with any other aspect or combination of aspects listed herein, a device or device system as described herein further comprise a signal analysis unit configured to analyze the signal of the scattered light with a forward angle and the signal of the fluorescent light for analyzing the particles and/or cells.

In accordance with a tenth aspect of the present disclosure, which may be used in combination with any other aspect or combination of aspects listed herein, a method of analyzing particles and/or cells in a measurement sample comprises: using a flow cell to form a sample flow of the measurement sample; using a light source to emit an irradiation light; using the irradiation light to illuminate the sample flow; using a collecting lens to collect both a scattered light with a forward angle and a fluorescent light from the particles and/or cells in the sample flow; and using one, two, or more detectors to detect a signal of the scattered light with a forward angle and a signal of the fluorescent light.

In accordance with an eleventh aspect of the present disclosure, which may be used in combination with any other aspect or combination of aspects listed herein, two separate detectors are used to detect the signal of the scattered light with a forward angle and the signal of the fluorescent light.

In accordance with a twelfth aspect of the present disclosure, which may be used in combination with any other aspect or combination of aspects listed herein, a method as described herein further comprises using a focusing module to focus the irradiation light to form an elliptical beam spot on the sample flow.

In accordance with a thirteenth aspect of the present disclosure, which may be used in combination with any other aspect or combination of aspects listed herein, the collected and/or detected scattered light includes a scattered light with a scattering angle less than about 3, 4, 5, 6, 7, 8, 9, 10, 11, 12, 13, 14, 15, 16, 17, 18, 19, 20, 21, 22, 23, 24, or 25 degrees In accordance with a fourteenth aspect of the present disclosure, which may be used in combination with any other aspect or combination of aspects listed herein, a method as described herein further comprises using a doublet lens to focus the collected fluorescent light.

In accordance with a fifteenth aspect of the present disclosure, which may be used in combination with any other aspect or combination of aspects listed herein, the flow cell is part of a cartridge device configured to be placed into a reader instrument for analysis, and wherein the reader instrument comprises a light source, a collecting lens, detectors, and a signal analysis unit.

In accordance with a sixteenth aspect of the present disclosure, which may be used in combination with any other aspect or combination of aspects listed herein, a method as described herein further comprises using the cartridge device to mix a sample with a reagent to form the measurement sample and to form a sample flow of the measurement sample in the flow cell.

In accordance with a seventeenth aspect of the present disclosure, which may be used in combination with any other aspect or combination of aspects listed herein, a method as described herein further comprises using a signal analysis unit to analyze the signal of the scattered light with a forward angle and the signal of the fluorescent light for analyzing the particles and/or cells.

In accordance with an eighteenth aspect of the present disclosure, which may be used in combination with any other aspect or combination of aspects listed herein, a method for analyzing particles and/cells in a sample, comprising: receiving the sample into a cartridge device comprising a flow cell; using the cartridge device to mix the sample the sample with a reagent to form a measurement sample; using the flow cell to form a sample flow of the measurement sample; using a light source to emit an irradiation light; using the irradiation light to illuminate the sample flow; using a collecting lens to collect both a scattered light and a fluorescent light from the particles and/or cells in the sample flow; and using one, two, or more detectors to detect a signal of the scattered light and a signal of the fluorescent light.

In accordance with a nineteenth aspect of the present disclosure, which may be used in combination with any other aspect or combination of aspects listed herein, the reagent comprises a fluorescence labeling compound.

In accordance with a twentieth aspect of the present disclosure, which may be used in combination with any other aspect or combination of aspects listed herein, two separate detectors are used to detect the signal of the scattered light and the signal of the fluorescent light.

In accordance with a twenty-first aspect of the present disclosure, which may be used in combination with any other aspect or combination of aspects listed herein, a method as described herein further comprises using a focusing module to focus the irradiation light to form an elliptical beam spot on the sample flow.

In accordance with a twenty-second aspect of the present disclosure, which may be used in combination with any other aspect or combination of aspects listed herein, the collected and/or detected scattered light includes a scattered light with a scattering angle less than about 3, 4, 5, 6, 7, 8, 9, 10, 11, 12, 13, 14, 15, 16, 17, 18, 19, 20, 21, 22, 23, 24, or 25 degrees.

In accordance with a twenty-third aspect of the present disclosure, which may be used in combination with any other aspect or combination of aspects listed herein, the collected and/or detected scattered light includes a scattered light with a scattering angle more than about 25, 30, 35, 40, 45, 50, 55, 60, 65, 70, 75, 80, 85, or 90 degrees.

In accordance with a twenty-fourth aspect of the present disclosure, which may be used in combination with any other aspect or combination of aspects listed herein, a method as described herein further comprises using a doublet lens to focus the collected fluorescent light.

In accordance with a twenty-fifth aspect of the present disclosure, which may be used in combination with any other aspect or combination of aspects listed herein, a method as described herein further comprises using a signal analysis unit to analyze the signal of the scattered light and the signal of the fluorescent light for analyzing the particles and/or cells.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

The disclosure claimed is:

1. A device system, comprising: a flow cell configured to form a sample flow of a measurement sample, wherein the measurement sample comprises particles or cells; a light source configured to emit an irradiation light for illuminating the sample flow; a collecting lens configured to collect both a scattered light with a forward angle and a fluorescent light from the particles or cells in the sample flow; and one, two, or more detectors configured to detect a signal of the scattered light with the forward angle and a signal of the fluorescent light; a receiving module configured to split the scattered light with a forward angle and the fluorescent light collected by the collecting lens into two separate optical paths toward two separate detectors, respectively.

2. The device system of claim 1, further comprising a focusing module configured to focus the irradiation light to form an elliptical beam spot on the sample flow.

3. The device system of claim 1, further comprising a focusing module that comprises a lens that is either not coaxial or not perpendicular with a central axis of the irradiation light.

4. The device system of claim 1, wherein a collected or detected scattered light comprises a scattered light with a scattering angle less than about 3, 4, 5, 6, 7, 8, 9, 10, 11, 12, 13, 14, 15, 16, 17, 18, 19, 20, 21, 22, 23, 24, or 25 degrees.

5. The device system of claim 1, wherein:
the flow cell is part of a cartridge device configured to be placed into a reader instrument for analysis; and
the reader instrument comprises the light source, the collecting lens, the detectors, and a signal analysis unit.

6. The device system of claim 5, wherein the cartridge device is configured to mix a sample with a reagent to form the measurement sample and to form a sample flow of the measurement sample in the flow cell.

7. The device of claim 6, wherein the reagent is a fluorescent labeling compound.

8. The device system of claim 1, further comprising a doublet lens configured to focus the collected fluorescent light.

9. The device system of claim 1, further comprising a signal analysis unit configured to analyze the signal of the scattered light with a forward angle and the signal of the fluorescent light for analyzing the particles or cells.

10. A method of analyzing particles or cells in a measurement sample, comprising: using a flow cell to form a sample flow of the measurement sample; using a light source to emit an irradiation light; using the irradiation light to illuminate the sample flow; using a collecting lens to collect both a scattered light with a forward angle and a fluorescent light from the particles or cells in the sample flow; using one, two, or more detectors to detect a signal of the scattered light with a forward angle and a signal of the fluorescent light; and using a receiving module configured to split the scattered light with a forward angle and the fluorescent light collected by the collecting lens into two separate optical paths toward two separate detectors, respectively.

11. The method of claim 10, wherein two separate detectors are used to detect the signal of the scattered light with a forward angle and the signal of the fluorescent light.

12. The method of claim 10, further comprising using a focusing module to focus the irradiation light to form an elliptical beam spot on the sample flow.

13. The method of claim 10, wherein the collected or detected scattered light comprises a scattered light with a scattering angle less than about 3, 4, 5, 6, 7, 8, 9, 10, 11, 12, 13, 14, 15, 16, 17, 18, 19, 20, 21, 22, 23, 24, or 25 degrees.

14. The method of claim 10, wherein the collected or detected scattered light comprises a scattered light with a scattering angle more than about 25, 30, 35, 40, 45, 50, 55, 60, 65, 70, 75, 80, 85, or 90 degrees.

15. The method of claim 10, further comprising using a doublet lens to focus the collected fluorescent light.

16. The method of claim 1, wherein:
the flow cell is part of a cartridge device configured to be placed into a reader instrument for analysis; and
the reader instrument comprises the light source, the collecting lens, the detectors, and a signal analysis unit.

17. The method of claim 16, further comprising using the cartridge device to mix a sample with a reagent to form the measurement sample and to form a sample flow of the measurement sample in the flow cell.

18. The method of claim 17, wherein the reagent is a fluorescence labeling compound.

19. The method of claim 10, further comprising using a signal analysis unit to analyze the signal of the scattered light with a forward angle and the signal of the fluorescent light for analyzing the particles or cells.

* * * * *